US006916631B2

(12) United States Patent
Burgeson et al.

(10) Patent No.: US 6,916,631 B2
(45) Date of Patent: Jul. 12, 2005

(54) B1K CHAIN OF LAMININ AND METHODS OF USE

(75) Inventors: Robert E. Burgeson, Marblehead, MA (US); David Wolfe Wagman, Melrose, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 10/841,139

(22) Filed: May 7, 2004

(65) Prior Publication Data

US 2004/0208881 A1 Oct. 21, 2004

Related U.S. Application Data

(60) Continuation of application No. 10/443,349, filed on May 22, 2003, which is a continuation of application No. 09/161,872, filed on Sep. 28, 1998, now abandoned, which is a continuation of application No. 08/735,893, filed on Oct. 23, 1996, now Pat. No. 5,914,317, which is a division of application No. 08/144,121, filed on Oct. 27, 1993, now Pat. No. 5,610,031.

(51) Int. Cl.$^7$ ....................... G12P 21/06; A62K 39/395; A07K 16/28

(52) U.S. Cl. ............... 435/69.3; 424/145.1; 530/388.24

(58) Field of Search ......................... 530/388.24, 387.3; 424/145.1; 435/69.3

(56) References Cited

U.S. PATENT DOCUMENTS 4,834,975 A * 5/1989 Siadak et al.
5,003,044 A 3/1991 Hunter et al.
5,610,031 A 3/1997 Burgeson et al.
5,914,317 A 6/1999 Burgeson et al.

FOREIGN PATENT DOCUMENTS

WO WO 92/17498 10/1992

OTHER PUBLICATIONS

Campbell A, General properties and applications of monoclonal antibodies, Elsevier Science Publishers, section 1.1, pp 1–32, 1984.*
Harlow E, Lane D., Antibodies a laboratory manual. Cold Spring Harbor, New York: Cold Spring Harbor Laboratory Press, 198 53–137.*
Gerecke et al. cDNAs Encoding for Two of the Chains of Anchoring Filament Proein Kalinin Show Similarity to the Laminin B1 and B2 Chains. Matrix Collagen and Related Research. 13:(1):20–21.*
Abaza MS, Atassi MZ. Effects of amino acid substitutions outside an antigenic site on protein binding to monoclonal antibodies of predetermined specificity obtained by peptide immunization: demonstration with region 94–100 (antigenic site 3) of myoglobin.*

Colman PM. Effects of amino acid sequence changes on antibody–antigen interactions. Res Immunol. 145(1):33–36, 1994.*

Lederman S, et al. A single amino acid substitution in a common African allele of the CD4 molecule ablates binding of the monoclonal antibody, OKT4. Mol Immunol. 28(11):1171–81, 1991.*

McMillan et al., "Ultrastructural Orientation of Laminin 5 in the Epidermal Basement Membrane: an Updated Model for Basement Membrane Organization, *The Journal of Histochemistry & Cytochemistry",* vol. 51, No. 10, pp. 1299–1306 (2003).

U.S. Appl. No. 08/141,233, filed Oct. 1993, Burgeson et al.

Aratani et al., "Enhanced Synthesis and Secretion of Type IV Collagen and Entactin during Adipose Conversion of 3T3–L1 Cells and Production of Unorthodox Laminin Complex" *The Journal of Biological Chemistry,* vol. 263, No. 31, pp. 16163–16169, (1988).

Beck et al., "Structure and Function of Laminin: Anatomy of a Multidomain Glycoprotein" *The FASEB Journal,* vol. 4, pp. 148–160, (1990).

Berger et al. (eds) "Guide to Molecular Cloning Techniques", *Meth. in Enzymology* 152:316–703 ((1987).

Cooper et al., "Studies on the Biosynthesis of Laminin by Murine Parietal Endoderm Cells" *European Journal of Biochemistry,* vol. 119, pp. 189–197, (1981).

Davis et al., "Isolation and Characterization of Rat Schwannoma Neurite–promoting Factor. Evidence that the Factor Contains Laminin" *The Journal of Neuroscience,* vol. 5, No. 10, pp. 2662–2671, (1985).

Edgar et al., "Structural Requirements for the Stimulation of Neurite Outgrowth by Two Variants of Laminin and Their Inhibition by Antibodies" *The Journal of Cell Biology,* vol. 106, pp. 1299–1306, (1988).

Ehrig et al., "Merosin, A Tissue–Specific Basement Membrane Protein, is a Laminin–Like Protein" *Proceedings of the National Academy of Sciences,* vol. 87, pp. 3264–3268, (1990).

Engvall et al., "Distribution and Isolation of Four Laminin Variants; Tissue Restricted Distribution of Heterotrimers Assembled From Five Different Subunits" *Cell Regulation,* vol. 1, pp. 731–740, (1990).

Engvall et al., "Mapping of Domains in Human Laminin Using Monoclonal Antibodies: Localization of the Neurite–promoting Site" *The Journal of Cell Biology,* vol. 103, No. 6, pp. 2457–2465, (1986).

Frenette et al., "Biosynthesis and Secretion of Laminin and Laminin–associated Glycoproteins by Nonmalignant and Malignant Human Keratinocytes: Comparison of Cell Lines from Primary and Secondary Tumors in the Same Patient" *Cancer Res,* vol. 48, pp. 5193–5202, (1988).

(Continued)

*Primary Examiner*—Christina Chan
*Assistant Examiner*—Maher Haddad
(74) *Attorney, Agent, or Firm*—Fish & Richardson P.C.

(57) ABSTRACT

Antibodies directed against laminin B1k are provided.

29 Claims, 13 Drawing Sheets

OTHER PUBLICATIONS

Gerecke et al., "cDNA's Encoding for the Three Chains of the Anchoring Filament Protein Kalinin Show Similarity to the Laminin A B1 and B2 Chains", *Mol. Biol. Cell*, vol. 3, (suppl.), p. # 1A, (1992).

Hunter et al., "Laminin Chain Assembly by Triple and Double Stranded Coiled–Coll Structures", *The Journal of Biological Chemistry*, vol. 267, No. 9, pp. 6006–6011, (1992).

Hunter et al., "Expression of S–Laminin and Laminin in the Developing Rat Central Nervous System" *The Journal of Comparative Neurology*, vol. 323, pp. 238–251, (1992).

Hunter et al., "An LRE (Leucine–Arginine–Glutamate)–dependent Mechanism for Adhesion of Neurons to S–laminin" *The Journal of Neuroscience*, vol. 11, No. 12, pp. 3960–3671, (1991).

Hunter et al., "Primary Sequence of a Motor Neuron–Selective Adhesive Site in the Synaptic Basal Lamina Protein S–Laminin" *Cell*, vol. 59, pp. 905–913, (1989).

Liesi et al., "Glial Cells of Mammalian Brain Produce a Variant Form of Laminin" *Experimental Neurology*, vol. 105, pp. 86–92, 1989.

Marinkovich et al., "The Anchoring Filament Protein Kalinin is Synthesized and Secreted as a High Molecular Weight Precursor", *The Journal of Biological Chemistry*, vol. 267, No. 25, pp. 17900–17906, (1992).

Marinkovich et al., "The Dermal–Epidermal Junction of Human Skin Contains a Novel Laminin Variant" *The Journal of Cell Biology*, vol. 119, No. 3, pp. 695–703, 1992.

Marinkovich et al., "Characterization of a Novel Laminin Isoform Produced by Human Keratinocytes *In Vitro*", *Clinical Research*, vol. 39, No. 2, pp. # 565A, (1991).

Morita et al., "Post–translational Assembly and Glycosylation of Laminin Subunits in Parietal Endoderm–like F9 Cells" *Biochemistry Journal*, vol. 229, pp. 259–264, (1985).

Paulsson et al., "Mouse Heart Laminin" *The Journal of Biological Chemistry*, vol. 264, No. 31, pp. 18726–18732, 1989.

Peters et al., "The Biosynthesis, Processing, and Secretion of Laminin by Human Choriocarcinoma Cells" *The Journal of Biological Chemistry*, vol. 260, No. 27, pp. 14732–14742, (1985).

Rouselle et al., "Kalinin: An Epithelium–Specific Basement Membrane Adhesion Molecule That is a Component of Anchoring Filaments" *Journal Cell Biology*, vol. 114, pp. 567–576, (1991).

Sanes et al., "S–Laminin" *Cold Spring Harbor Symposia on Quantitative Biology*, vol. 55, pp. 419–430, (1990).

Wewer et al., "Human Laminin isolated in a Nearly Intact, Biologically Active Form from Placenta by Limited Proteolysis" *The Journal of Biological Chemistry*, vol. 258, No. 20, pp. 12654–12660, (1983).

Woodley et al., "Laminin Inhibits Human Keratinocyte Migration" *Journal of Cellular Physiology*, vol. 136, pp. 140–146, (1988).

Gerecke et al., "cDNAs Encoding for Two of the Chains of the . . . ", Matrix 13:20–21, Jan. 1993.

* cited by examiner

DOMAIN VI

```
Blk    1   QQACSRGACYPPVGDLLVGRTRFLRASSTCGLTKPETYC  TQYGEWQMKCCKCDSRQPH   NYYSHRVE
             :|   |||:  ||||::||      |       ||||  ||| ||   : :|| |:|:|   ||  ::||
Ble    1   OEPEFSYGCAEGSCYPATGDLLIGRAQKLSVTSTCGLHKPEPYCIVGHLQE DKKCFICNSQDPYHETLNPDSHLIE

Blk   67   NVASSSGPMR    WMQSQNDVNPVSLQLDLDRRFQLQEVMMEFPGAHAAGMLIERSSDFGKTHRVYQYLAADCTSTF
            ||  :|        |||:|:|: | :|||  |::   |:|    ::|:||||||||||||||||| |: |: |    |
Ble   77   NVVTTFAPNRLKIWMQSENGVENVTIQLDLEAEFFTHLIMTFKTFRPAAMLIERSSDFGKTWGVYRYFAYDCEASF

Blk  141   PRVRQGRPQSWQDVRCQSLPQRPNARLNGGKVQLNLMDLVSGIPATQSKIQEVGEITNLRVNFTRLAPV     P
             |:       ::   |:| ||      ::|:        |     |      |  :||::     |  |::  | :|
Ble  154   PGISTGPMKKVDDIICDS RYSDIEPSTEGEVIFRALDPAFKIEDPYSPRIQNLIKITNLRIKFVKLHTLGDNLLDS

Blk  212   KLDHPPSAYYAVSQLRLQGS
             :::      ||||  :: :|
Ble  230   RMEIREKYYYAVYDMVVRGN
```

FIG. 3A

DOMAIN III / V

```
Blk  288  GQDAHECQRCDCNGHSENCHFDPAVFAASQGAYGGVCDNCRDHTEGKNCERCQLHYFRNRRPGASIQETCISCECDP
          ||| ||| ||  :  : :|:||:||      ||||:|   :|  ||||:|    |:: :  :   |  : ||| |
Ble  305  GRNSNACKKCNCNEHSISCHFDMAVYLATGNVSGGVCDDCQHNTMGRNCEQCKPFYYQHPERDIRDPNFCERCTCDP

Blk  365  DGQWAGAPCDP          VTGQCVCKEHVQGERCDLCKPGFTGLTYANPQGCHR
          :  ||   ||            : ||| ||   :|:||:|| ||  |  :   :| ||
Ble  382  AGSQNEGICDSYTDFSTGLIAGQCRCKLNVEGE

DOMAIN II

```
Blk   423  PCDEESGRCICLPNVGGPKCDQCAPYHMKLASGQGCEPCACDPHNSLSPQCNQFTGQCPCREGFGGLMCS
           ||   | |||||||    |  |  ||||  ||||  | |||   :|::| |||||||| |   |||  ||
Ble  1017  HCNGSDCQCDKATGQCLCLPNVIGQNCNCDRCAPNTMQLASGTGCDPCNCNAAHSFGPSCNEFTGQCQCMPGFGGRTCS

Blk   493  AAAIRQCPDRTYGDVATGCRACDCDEFRGTEGPGCDKASG  VLCRPGLTGPRCDQCQRGYCNRYPVCVA  CHPCFQTY
           :|  :||    |: :||||||||   |||||||     |  :|   :| |||||| |:|:| |||:: |||  |
Ble  1094  ECQELFWGDPDVECRACDCDPRGIETPQCDQSTGQCVCVEGPRCDKCTRGYSGVFPDCTP  CHQCFAIW

Blk   568  DADLREQALRFGRLPNATASLWSGPGLEDRGLASRILDAKSKIEQIRAVL  SSPAVTEQEVAQVASAILSLRRTIQ
           |   :   |  :||  |      : |    :    ::        |  |                |::    :
Ble  1165  DVIIAELTNRTHRFLEKAKALKISGVIG  PYRETVDSVERKVSEIKDILAQSPAAEPLKNIGNLFEEAERMLIKDVT

Blk   643  GL  QLDIPLEEET      LSLPRDLESLDRSFNGLLITMYQRKREQFEKISSADPSGAFRMLSTAYEQSAQAAQQVS
           ::   |:::| | |      |::::|:||:  |  :|
Ble  1240  EMMAQVEVKLSDTTSQSNSTAKEIDSLQTEAESLDNTVKELAEQLEEFIKNSDIRGALDSITKYFQMSLEAEERVNAS

Blk   713  DSSRLLDQLRDSRREAERLVRQAGGGGGTGSPKLVA    LRLEMSSLPDLTPTFNKL
           :|  :    |:::|::  |   ::    ::  |  |   |:::|    :::|
Ble  1317  TTEPNSTVEQSALMRDRVEDVMERESQFKEKQEEQARLLDELAGKLQSLDLSAAAEMT
```

FIG. 3C

```
                                                                                                   CGNSRQMACTP
                                                                                                   ||       ||
                                                                                                   CGTPPGASCSE
                    DOMAIN I
       ALPHA DOMAIN
Blk  778 ISCPGELCPQDNG   TACASRC IRGVLPRAGGAFLMAGQVAEQLRASMPAPA TRQMIRAAEESASQIQSSAQRLET
         ||   ||   ||:|          |::  |  |  |   ||  |::  :::          |:   |:   |  ::
Ble 1387 TECGGPNCRTDEGERKCGGPGC  GGLVTVAHNWQKAMDLDQDVLSALAEVEQLSKMVSEAKLRADEAKQSAEDILL

Blk  851 QVSASRSQMEEDVRRITRLLIQQVRDFLITDPDTDAATIQEVRRAVLALMLPTDSATVLQKMNEIQAIAARLPNVDLVL
         |: :|   | |       |  |:|:||:|||:           |: |   ||::  :|              |:::||
Ble 1463 KTNATKEKMDKSNEELRNLIKQIRNFLTQDSADLDSIEAVANEVLKMEMPSTPQQLQNLTEDIRERVESLSQVEVIL

Blk  928 SQTKQDIGGARRLQAEAEEARSRAHAVEGQVEDVVGNLRQ          GTVALQEAQDTMQGTSRSLRLIQDRVAEVQ
         : |   ||: ||  |   |  |        |::|   |             |:  ||   |   :||  |    |   |
Ble 1540 QHSAADIARAEMLIEEAKRIASKSATDVKVTADMVKEALEEAEKAQVAAEKAIKQADEDIQGTQNLLTSIESETAASE

Blk  998 QVLGQQKLVTSMTKQLGDFWTRMEELRHQARQQGAEAVQAQQLAEGASEQALSAQEGFE  RIKQKYAELKDRLGQSS
         : |          ::::   :|||| |||  |   :||    ::  |  :                         ::
Ble 1617 ETL        FNASQRISELERNVEELKRKAAQNSGEAEYIERVVYTVKQSAEDVKKTLDGELDERYKKVENLIAKKT
                                                                        (SEQ.I.D.NO.3)
Blk 1074 MLGEQQGAR  IQSVKTEAEELFGETMEMMDRMKDMELELLRAAGH HAALSDLTGLEKRVEQIRDHINGRVLYYSTCK
         : :::  |:|          ||  ||  |::        ::: ||:|          :|  |  :    :|   ||||
Ble 1688 EESADARRKAEHLQNEAKTLLAQANSKLQLLRDLERRKYEDNQRYLEDKAQELARLEGEVRSLLRDISQKVAVYSTCL
                                                                        (SEQ.I.D.NO.1)
```

*FIG. 3D*

```
Blk    1                          QQA*SR*A**PVVTRF*RAS***T*T****TQYG*WQMCK*RQ
Ble^   1     QEPEFSYGCAEGSCYPATGDLLIGRAQKLSVTSTCGLHKPEPYCIVSHLQE DKKCFICNSQD
Bls>   1     QVPSLDVPSR*******V*DR*TAS******S*Q******D E**L*D*RR

Blk  57     *H    *YYRV*ASSSG*M*     ****Q*D*NP*SL***DRR*QLQEVM*E*PGAHA*G
Ble  64     PYHETLNPDSHLIENVVTTFAPNRLKIWWQSENGVENVTIQLDLEAEFHFTHLIMTFKTFRPAA
Bls  65     *FSARDNRIQ**S*Q*RTA*******PM*******************

Blk 114     *********RQ*L*ATSTR*VRQ*RPQSWQ*VR*Q*LPQRPNARLNG*K*QLNLM
Ble 128     MLIERSSDFGKTWGVYRYFAYDCEASFPGISTGPMKKVDDIICDS RYSDIEPSTEGVIFRAL
Bls 129     V*A**RR***SG*D****PLA*PRRW**VV*E*****Y*V*

Blk 178     *LVSG**ATQ*QKEVGE******APV     PKLDHPPSA**SQLRLQ*S*SEQ.I.D.NO.5)
Ble 191     DPAFKIEDPYSPRIQNLLKITNLRIKFVKLHTLGDNLLDSRMEIREKYYYAVYDMVVRGN(SEQ.I.D.NO.6)
Bls 192     ***IP*P***S*************VNLTR************P*R*********L*EL*I** (SEQ.I.D.NO.7)
```

^PIKKARAINEN et al, 1987
>HUNTER et al, 1989

FIG. 5

RAT LAMBIS* RES.#1637    EALKLKRAGNSLAASTAEETAGSAQSRAREAEKQLREQVG (SEQ.I.D.NO.8)
                         ||||||||||||||||||||||  |||   |
HUMAN LAMBIS PEPTIDE     AGNSLAASTAEETAGSAQGRAQEA (SEQ.I.D.NO.9)

HUMAN LAMB1K RES.#1021   EELRHQARQQGAEAVQAQQLAEGASEQALSAQEGFERIKQ (SEQ.I.D.NO.10)
                          ::  :::::  :

HUMAN LAMB2T^ RES.#428   TGDCYSGDENPDIECADCPIGFYNDPHDPRSCKPCPCHNG (SEQ.I.D.NO.11)
                                 |||||||||||||||||
HUMAN LAMB2T PEPTIDE             DENPDIECADCPIGFYN (SEQ.I.D.NO.12)

HUMAN LAMB2T^ RES.#1083  KVDTRAKNAGVTIQDTLNTLDGLLHLMDQPLSVDEEGLVL (SEQ.I.D.NO.13)
                              ||||||||||||||||||||||||||||
HUMAN LAMB2T PEPTIDE          NAGVTIQDTLNTLDGLLHLMDQPLS (SEQ.I.D.NO.14)

*HUNTER ET AL, 1989
^KALLUNKI ET AL, 1992

*FIG. 6*

|  | PERCENT IDENTITY | PERCENT SIMILARITY |
|---|---|---|
| HUMAN LAMININ B1e | 34.1 | 53.6 |
| HUMAN LAMININ B2e | 28.4 | 49.6 |
| HUMAN LAMININ B2t | 21.4 | 43.1 |
| RAT LAMININ B1s | 37.1 | 56.2 |

*FIG. 7*

B1K CHAIN OF LAMININ AND METHODS OF USE

RELATED APPLICATIONS

This application is a continuation of U.S. application Ser. No. 10/443,349, filed May 22, 2003, which is a continuation of U.S. application Ser. No. 09/161,872, filed Sep. 28, 1998, now abandoned, which is a continuation of U.S. application Ser. No. 08/735,893, filed Oct. 23, 1996, now U.S. Pat. No. 5,914,317, which is a divisional of U.S. Ser. No. 08/144,121, filed on Oct. 27, 1993, now U.S. Pat. No. 5,610,031, the disclosures of which are incorporated herein by reference in their entirety.

GOVERNMENT SUPPORT

This invention was made with government support. The U.S. government may have certain rights in this invention.

BACKGROUND OF THE INVENTION

The present invention relates to adhesion proteins and to methods of using them, e.g., to promote the adhesion of cells to a substrate, e.g., to human dermis. In particular, overlapping cDNA clones encoding the entire laminin B1k chain and recombinant proteins expressed therefrom are disclosed.

The structure of the prototype laminin, a glycoprotein component of most, if not all, basement membranes has been well described in a number of species. Its overall appearance, as visualized by rotary shawdowing, is cross-shaped with a single long arm arising from the coiled-coil interaction of three separate polypeptide chains and three short arms, each originating from the individual polypeptide chains. The three chains are: A, typified by the Ae chain of EHS laminin (400-kD); B1, typified by the B1e chain of EHS laminin (220-kD); and B2, typified by the B2e chain of EHS laminin (210-kD) chains. The primary structure for each of the three prototypic polypeptide chains in humans has been elucidated by overlapping cDNAs.

Additional polypeptides that are related to the laminin chains have been identified. A rat B1 chain homologue, s-laminin (B1s), has been identified. A human A chain homologue, merosin (Am), has been described and is the same as a homologue A chain found in mouse and bovine heart. Both chains can combine with the laminin A, B1 or B2 chains to form the variant trimeric proteins [Ae, B1s, B2e], [Am, B1e, B2e] and [Am, B1s]. A second B1 variant (the sequence of which is a chain based on partial cDNA sequences) from avian eye has been reported and overlapping cDNAs for a human variant B2 chain called laminin B2t have also been described.

Kalinin is an epithelium-specific laminin variant that is the major, if not the only component of the anchoring filament. (The anchoring filament is a characteristic ultra-structural component of the dermal-epidermal junction of skin believed to mediate the adhesion of the epithelium to the basement membrane.) The kalinin molecule contains three disulfide bond-linked polypeptide chains consisting of a 200-kD kalinin A chain (Ak), a 155-kD kalinin B2 chain (B2t), and a 140-kD kalinin B1 chain (B1k). Rotary shadowing of the molecule results in a 107-nm rod with globular domains at each end.

Kalinin is an epithelial-specific cell attachment factor utilized by skin keratinocytes for strengthening their attachment to the underlying dermis. Antibodies to the Ak chain cause the detachment of subconfluent karatinocytes from their growth substrate and deepithelization of intact skin.

SUMMARY OF THE INVENTION

In general, the invention features a purified DNA including a sequence encoding a B1k chain of laminin.

In preferred embodiments: the DNA encodes the B1k protein of (SEQ ID NO:2); the encoded B1k peptide is at least 80, more preferably 90, and most preferably 95 or 98% homologous with the sequence of (SEQ ID NO:2); the DNA encodes a biologically active B1k.

In another aspect, the invention features a recombinant B1k.

In preferred embodiments: the recombinant B1k protein has the sequence of (SEQ ID NO:2); the recombinant B1k peptide is at least 80, more preferably 90, and most preferably 95 or 98% homologous with the sequence of (SEQ ID NO:2); the recombinant B1k has biological activity.

The invention also includes a vector including a DNA sequence encoding a B1k protein; a cell containing the vector; a method for manufacture of B1k including culturing the cell in a medium to express B1k.

In another aspect, the invention features a purified DNA including (or consisting essentially of) a sequence encoding a fragment of a B1k laminin chain.

In preferred embodiments: the sequence encodes domain VI of B1k, or a kalinin A chain-binding fragment thereof; the sequence encodes a peptide with a biological activity of domain VI of native B1k, e.g., the ability to bind to a kalinin A chain; the sequence encodes any of domain VI, V, IV, IV, III, α, or I of B1k.

In other preferred embodiments: the sequence of the encoded B1k fragment is essentially the same as that of a naturally occurring B1k sequence; the DNA sequence which encodes the B1k fragment is at least 85%, more preferably at least 90%, yet more preferably at least 95%, and most preferably at least 98 or 99% homologous with DNA encoding a naturally occurring B1k, e.g., B1k encoding DNA from SEQ ID NO:1; the sequence which encodes a B1k fragment hybridizes under high or low stringency to a nucleic acid which encodes a naturally occurring B1k sequence e.g., the amino acid sequence of SEQ ID NO:1; the amino acid sequence of the encoded B1k fragment is less than 30, more preferably less than 40, more preferably less than 50, and most preferably less than 60, 80, 100, or 200 amino acid residues in length; the encoded B1k amino acid sequence is at least 50% more preferably 60%, more preferably 70%, more preferably 80%, more preferably 90%, and most preferably 95% as long as a naturally occurring B1k; the amino acid sequence of the encoded B1k fragment is at least 80%, more preferably at least 85%, yet more preferably at least 90%, yet more preferably at least 95%, and a most preferably at least 98 or 99% homologous with a naturally occurring B1k sequence, e.g., the sequence of SEQ ID NO:1; the fragment has biological activity.

In other preferred embodiments the fragment includes more than one B1k domain and: the domains in the encoded peptide are arranged in the same relative linear order as found in a naturally B1k; the linear order of the encoded domains is different from that found in a naturally occurring B1k; the domains in the encoded peptide differ in one or more of composition (i.e., which domains are present), linear order, or number (i.e., how many domains are present or how many times a given domain is present) from a naturally occurring B1k.

In another aspect, the invention features, a DNA, preferably a purified DNA, which includes (or consists essentially of) a sequence encoding a fragment of B1k of 20 or more amino acids in length, the peptide having at least 90% homology with an amino acid sequence which is the same, or essentially the same, as a naturally occurring B1k peptide, e.g., the amino acid sequence of SEQ ID NO:2. In preferred embodiments the purified DNA encodes: a peptide which is at least 30, more preferably at least 40, more preferably at least 50, and most preferably at least 60, 80, 100, or 200, amino acid residues in length; the encoded peptide is at least 50% more preferably at least 60%, more preferably 70%, more preferably 80%, more preferably 90%, and most preferably 95% as long as a naturally occurring B1k; a peptide which is at least 80, more preferably at least 85, yet more preferably at least 90, yet more preferably at least 95, and most preferably at least 98 or 99% homologous with an amino acid sequence which is the same, or essentially the same, as a naturally occurring B1k peptide, e.g., the amino acid sequence of SEQ ID NO 2; the peptide has biological activity.

The invention also includes a DNA sequence encoding a B1k fragment; a cell containing the purified DNA; a method for manufacture of a B1k fragment comprising culturing the cell in a medium to express the B1k fragment.

In another aspect, the invention features a peptide which is a fragment of a B1k laminin chain.

In preferred embodiments: the peptide includes (or consists essentially of) domain VI of B1k or a kalinin A chain-binding fragment thereof; the peptide has a biological activity of domain VI of native B1k, e.g., the ability to bind to a kalinin A chain; the peptide includes any of domain VI, V, IV, III, II, α, or I of B1k; the fragment has biological activity.

In other preferred embodiments: the sequence of the peptide is essentially the same as that of a naturally occurring B1k sequence; the DNA sequence which encodes the B1k peptide is at least 85%, more preferably at least 90%, yet more preferably at least 95%, and most preferably at least 98 or 99% homologous with DNA encoding a naturally occurring B1k, e.g., B1k encoding DNA from SEQ ID NO:1; the sequence which encodes the B1k peptide hybridizes under high or low stringency to a nucleic acid which encodes a naturally occurring B1k sequence e.g., the amino acid sequence of SEQ ID NO:2; the amino acid sequence of the peptide is less than 30, more preferably less than 40, more preferably less than 50, and most preferably less than 60, 80, 100, or 200 amino acid residues in length; the peptide's amino acid sequence is at least 50% more preferably 60%, more preferably 70%, more preferably 80%, more preferably 90%, and most preferably 95% as long as a naturally occurring B1k; the amino acid sequence of the peptide is at least 80%, more preferably at least 85%, yet more preferably at least 90%, yet more preferably at least 95%, and a most preferably at least 98 or 99% homologous with a naturally occurring B1k sequence, e.g., the sequence of SEQ ID NO:2.

In other preferred embodiments the peptide includes more than one B1k domain and: the domains in the peptide are arranged in the same relative linear order as found in a naturally B1k; the linear order of the domains is different from that found in a naturally occurring B1k; the domains in the peptide differ in one or more of composition (i.e., which domains are present), linear order, or number (i.e., how many domains are present or how many times a given domain is present) from a naturally occurring B1k; the peptide has biological activity.

In another aspect, the invention features a transgenic animal, e.g., a rodent, having a B1k transgene, e.g., a transgene which misexpresses the B1k chain of laminin.

In another aspect, the invention features a method of increasing the permeability of the skin including inhibiting an interaction between B1k and a second molecule, e.g., a kalinin A chain.

In preferred embodiments, the interaction is inhibited by: administering an antibody against a site on kalinin A with which B1k interacts; administering an antibody against a site on B1k, e.g., a site in domain VI, which interacts with the second molecule; administering a fragment of B1k, e.g., a fragment containing domain VI which competes, e.g., competitively or non-competitively with B1k for a site on the second molecule.

In another aspect, the invention features a method of promoting the adhesion of a molecule, e.g., kalinin A or kalinin A-containing molecule, e.g., kalinin or laminin or a cell, e.g., a keratinocyte, to a substrate including providing the substrate coupled, linked, or adhered, to a fragment of B1k which includes domain VI, contacting the molecule or cell, with the B1k domain VI.

In preferred embodiments, the method further includes forming a covalent bond, e.g., a sulfhydral bond, between the molecule or cell and the B1k domain VI.

In another aspect, the invention features a peptide useful for promoting the adhesion of a first molecule or cell, e.g., a keratinocyte, to a second molecule or cell, e.g., a keratinocyte, including a first B1k domain linked to a second B1k domain. (The first domain, e.g., domain VI, binds to the first molecule or cell and the second domain, e.g., domain VI, binds to the second molecule or cell).

In another aspect, the invention features a method of coupling a first molecule or cell to a second molecule or cell including providing a molecule having a first B1k domain and a second B1k domain, linking the first molecule or cell to the first domain, and linking the second molecule or cell to the second domain.

In preferred embodiments: the first and/or second molecule is an adhesion molecule, e.g., laminin, kalinin, or collagen; the first and/or second B1k domain is domain VI or a kalinin A chain-binding fragment thereof of B1k; the first and/or second cell in a keratinocyte.

The invention also includes substantially pure preparation of an antibody, preferably a monoclonal antibody directed against a B1k protein or a fragment of a B1k protein, e.g., a fragment which contains only one domain of B1k; a therapeutic composition including an B1k protein or fragment thereof and a pharmaceutically acceptable carrier; a therapeutic composition which includes a purified DNA of the invention and a pharmaceutically acceptable carrier.

In another aspect, the invention features a method for treating an animal, e.g., a human, a mouse, a transgenic animal, or an animal model for a disorder, e.g., a disorder of the dermis, e.g., epidermal bulosis, including administering a therapeutically-effective amount of a B1k or fragment thereof to the animal.

In another aspect, the invention features a method for treating an animal, e.g., a human, a mouse, a transgenic animal, or an animal model for a disorder, e.g., a disorder of the dermis, e.g., epidermal bulosis, including administering to the animal cells selected, e.g., selected in vitro, for the expression of a product of the B1k gene, e.g., cells transformed with B1k or B1k fragment-encoding DNA.

In preferred embodiments: the cells are taken from the animal to which they are administered; the cells are taken from an animal which is MHC matched with the animal to which they are administered; the cells are taken from an animal which is syngeneic with the animal to which they are administered; the cells are taken from an animal which is of the same species as is the animal to which they are administered.

In another aspect, the invention features a method for treating an animal, e.g., a human, a mouse, a transgenic animal, or an animal model for a disorder, e.g., a disorder of the dermis, e.g, epidermal bulosis, including administering to the animal a nucleic acid encoding a B1k or fragment thereof and expressing the nucleic acid.

In another aspect, the invention features a method of evaluating the effect of a treatment, e.g., a treatment designed to promote adhesion of a keratinocyte to its substrate including carrying out the treatment and evaluating the effect of the treatment on the expression of the B1k gene.

In preferred embodiments the treatment is administered: to an animal, e.g., a human, a mouse, a transgenic animal, or an animal model for a dermal disorder, e.g., epidermal bulosis, or to a cell, e.g., a cultured cell.

In another aspect, the invention features a method for determining if a subject, e.g., a human, is at risk for a disorder related to mis-expression of the B1k gene, e.g., a disorder of the dermis, e.g., epidermal bulosis, including examining the subject for the expression of the B1k gene, non-wild type expression or mis-expression being indicative of risk.

In another aspect, the invention features a method for determining if a subject, e.g., a human, is at risk for a disorder related to mis-expression of the B1k gene, e.g., a disorder of the dermis, e.g., epidermal bulosis, including providing a nucleic acid sample from the subject and determining if the structure of an B1k gene allele of the subject differs from wild type.

In preferred embodiments: the determination includes determining if an B1k gene allele of the subject has a gross chromosomal rearrangement; the determination includes sequencing the subject's B1k gene.

In another aspect, the invention features, a method of evaluating an animal or cell model for a disorder, e.g., a disorder of the dermis, e.g., epidermal bulosis, including determining if the B1k gene in the animal or cell model is expressed at a predetermined level or if the B1k gene is mis-expressed. In preferred embodiments: the predetermined level is lower than the level in a wild type or normal animal; the predetermined level is higher than the level in a wild type or normal animal; or the pattern of isoform expression is altered from wildtype.

In another aspect, the invention features a transgenic rodent, e.g., a mouse, having a transgene which includes an B1k gene or B1k protein encoding DNA. In preferred embodiments: the B1k gene or DNA includes a deletion, e.g. a deletion of all or part of B1k, e.g., a deletion of all or part of a domain e.g., domain VI, or is otherwise mis-expressed.

Purified DNA is DNA that is not immediately contiguous with both of the coding sequences with which it is immediately contiguous (i.e., one at the 5' end and one at the 3' end) in the naturally occurring genome of the organism from which the DNA of the invention is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA or a genomic DNA fragment produced by PCR or restriction endonuclease treatment) independent of other DNA sequences. It also includes a recombinant DNA which is part of a hybrid gene encoding additional polypeptide sequence.

Homologous refers to the degree of similarity in sequence between two polypeptide molecules or between two nucleic acid molecules. When a position in both of the two compared sequences is occupied by the same base or amino acid monomeric subunit, e.g., if a position in each of two DNA molecules is occupied by adenine, then the molecules are homologous at that position. The homology between two sequences is a function of the number of matching or homologous positions shared by the two sequences. For example, 6 of 10, of the positions in two sequences are matched or homologous then the two sequences are 60% homologous. By way of example, the DNA sequences ATTGCC and TATGGC share 50% homology.

A transgene is defined as a piece of DNA which is inverted by artifice into a cell and becomes a part of the genome of the animal which develops in whole or part from that cell. Such a transgene may be partly or entirely heterologous to the transgenic animal.

A transgenic animal, e.g., a transgenic mouse, is an animal having cells that contain a transgene, which transgene was introduced into the animal, or an ancestor of the animal, at a prenatal, e.g., an embryonic stage.

A substantially pure preparation of a peptide is a preparation which is substantially free of the peptides with which it naturally occurs in a cell. A substantially pure preparation of a non-naturally occurring peptide is one which is at least 10% by weight of the peptide of interest.

Mis-expression, as used herein, refers to a non-wild type pattern of gene expression. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild-type in terms of the tissue specificity of expressions, e.g., increased or decreased expression (as compared with wild-type) in a predetermined cell type or tissue type; a pattern of expression that differs from wild type in terms of the length, amino acid sequence, post-translational modification, or a biological activity of a B1k gene product; a patterns of expression that differs from wild-type in terms of the effect of an environmental stimulus or extracellular stimulus on expression of the gene, e.g., a pattern of increased or decreased expression (as compared with wild type) in the presence of an increase or decrease in the strength of the stimulus; or a pattern of isoform expression which differs from wild-type.

A protein or peptide has B1k biological activity if it has one or more of the following properties: the ability to covalently bind via disulfide bond formation with a kalinin B2 chain and a kalinin A chain to form a trimeric protein, kalinin; the ability to bind the kalinin A chain through a covalent disulfide bond formation with domain VI of the B1k chain; the ability to specifically bind type IV collagen; if a B1k domain present on a B1k protein or fragment has a biological property that the domain has when present in the native B1k molecule, e.g., the ability to bind or associate in a specific way with another molecule, e.g., another laminin or kalinin chain or the ability to form a characteristic native rotary shadowy structure characteristic of native B1k.

The molecules of the invention are useful for promoting adhesion of adhesion molecules or keratinocytes to a substrate, e.g., human dermis. The molecules of the invention are also useful for research in cell adhesion. The role of the DNA sequence encoding a peptide having B1k activity and its products can be studied in cells, e.g., cultured cells, transformed with the aforementioned DNA sequence, or fragments thereof, or in transgenic animals. The peptides fragments of the invention allow preparation of antibodies, i.e., monoclonal antibodies, directed against a specific domain.

Other features and advantages of the invention will be apparent from the following description and from the claims.

BRIEF DESCRIPTION OF THE DRAWINGS

FIGS. 2–2C is a map of the nucleotide sequence of the laminin B1k chain (SEQ ID NO: 1) and the predicted amino acid sequence (SEQ ID NO: 2) of the B1k peptide chain. Triangles indicate potential N-linked glycosylation sites. Stars indicate potential glycosaminoglycan attachment sites. Potential O-linked glycosilation sites are underlined.

FIGS. 3A–3D, is a domain-by-domain comparison of the amino acid sequences of the laminin B1k chain (SEQ ID NO: 3) and the human B1 (SEQ ID NO: 4) chain (B1e).

FIG. 5 is a comparison of the amino acid sequences of domain VI for B1k (SEQ ID NO: 5), B1e (SEQ ID NO: 6), and B1s (SEQ ID NO: 7). The underlined regions are areas where the sequence identity between B1e and B1s is above average, but the sequence identity with B1 is considerably less than average. The arrow shows an additional cysteine contained by B1k at residue number 50.

FIG. 6 is a comparison of peptide sequences of rat laminin B1s (SEQ ID NO: 8), human laminin B1s (SEQ ID NO: 9) and human laminin B1k (SEQ ID NO: 10). Also shown is a comparison of the amino acid sequences of human laminin B2t peptides determined by deduction from cDNA (SEQ ID NO: 11 and SEQ ID NO: 13) (top line) and from sequencing of purified peptide (bottom line) (SEQ ID NO: 12 and SEQ ID NO: 14).

FIG. 7 is a comparison of the cloned cDNA sequence to the B1 and B2 chains of laminin (LAMB1e and LAMB2e), the B2 chain of kalinin (LAMB2t) and the B1 chain of s-laminin (LAMB1s).

DETAILED DESCRIPTION cDNA Clones for the Kalinin B1 (Laminin B1k) Chain

The screening of the squamous cell carcinoma cell cDNA expression library with a polyclonal antibody which recognizes human kalinin yielded several positive clones. The fusion proteins from positive clones were adsorbed to nitrocellulose and exposed to the polyclonal antiserum used for the initial screening. Antibodies binding the fusion proteins were individually collected and used for Western blot analysis of partially purified kalinin. Clones were identified that expressed fusion proteins that bound antibodies specific for the 140-kD and the 155/105-kD chain. (The B2 chain is processed from a 155 to a 105 kD form.) Selected clones were sequenced and the predicted amino acid sequences encoded by the cDNAs showed extensive homologies with the B1 and B2 laminin chains. The encoded sequences fro the B1k and B2t chains were confirmed by direct amino acid sequencing of the 140-kD and 155/105-kD kalinin chains.

The nucleotide sequences of the 155/105-kD chain were 99.9% identical to the recently published B2t chain and 100-kD chain of nicein. Protein sequencing of two tryptic peptides from the chain exactly matched derived amino acid sequences, confirming that laminin B2t, the 100-kD nicein chain and the 155/105-kD kalinin chain are identical.

Figure 1:
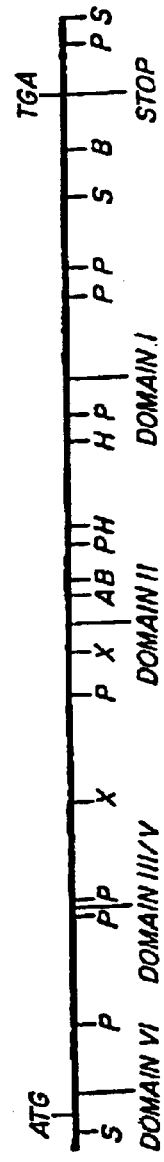
FIG. 1 is a map of the B1k region showing (heavy line) start (ATG) and stop codons (TGA), restriction sites (single letter abbreviations), and domains. The light lines below the map show overlapping cDNA clones encoding the entire kalinin B1 chain.

Clones encoding the kalinin 140-kD kalinin B1 chain were selected for further characterization (Kal26, Kal45, Kal48, Kal68, Kal82, and Kal85, FIG. 1). These clones contained 1.5-kb, 0.9-kb, 1.3-kb, 1.8-kb, 1.2-kb, and 2.1-kb inserts, respectively, and nucleotide sequencing demonstrated that the derived amino acid sequences showed extensive similarity to human laminin B1 chain. Rescreening of the cDNA library with Kal45 resulted in the isolation of clones Kal5-5 and Kal6-4 (FIG. 1). These clones contained 2.3-kb and 1.0-kb inserts, respectively. To obtain the 3' end of the cDNA, a 3' RACE procedure (BRL) was used on total mRNA from squamous cell carcinoma media. This resulted in the clone Kal92-1 (1.8-kb). The complete nucleotide sequence of the overlapping clones and the predicted amino acid sequence are shown in FIG. 2.

The immunogen for polyclonal antiserum against kalinin purified from human keratinocyte-conditioned culture medium has been previously described (Lunstrum et al., 1986; Rousselle et al., 1991).

Isolation of RNA and cDNA synthesis were performed as follows. Ten Costar T-225 flasks were seeded with squamous carcinoma cells (SCC) and allowed to grow until subconfluent. Media was removed and the cells were lysed and total RNA isolated following the guanidium thiocyanate method of Chomczynski and Sacchi, 1987. Poly A+RNA was collected using a Collaborative Research oligo dT Cellulose type 3 column and following company guidelines. Six hundred mg of Poly A+ enriched RNA was sent to Clontech Laboratories (Palo Alto, Calif.) for construction of the Lambda gt11 cDNA library using random primers.

Library screening was performed as follows. The anti-kalinin polyclonal antibody (pAB) was diluted in 1:10 in 10 mM TNT (Tris-HCl, pH 8.0; 150 mM NaCl; 0.05% Tween 20; 3% BSA). E. coli (Y-1090 strain) whole cell lysate was added to the diluted antibody and incubated at 4° C. for 24 hours on a nutator. The pre-absorbed antibody was centrifuged at 10,000 rpm for 10 minutes at 4° C. and the supernatant collected. The absorbed antibody was then diluted 1:10 (final dilution 1:100) in TBST (50 mM Tris-HCl, pH 7.9; 150 mM NaCl; 0.05% Tween 20) and 1.2% BSA added. The diluted absorbed antibody was used to screen $8.34 \times 10^5$ plaques from the unamplified random-primed cDNA library and horseradish peroxidase (HRP) secondary antibody was used to visualize the positive plaques. A total of 89 positive individual plaques were purified in a larger scale and tested again against the antibody.

Epitope determination for phage clones were performed as follows. For each clone, three 150×15 mm LB-ampicillin plates were plated at a density of 6000 pfu and grown 3 hours at 37° C. The plates were overlaid with IPTG saturated nitrocellulose filters and incubated overnight at 37° C. Plates were cooled at 4° C. for 15 minutes and the filters were removed and washed 3 times in TBST (15 min for each wash). The filters were blocked in 4% BSA in TBST for 1 hour at room temperature (RT). Filters were then washed 3 times in TBST. Filters were exposed to the pAB for 3–4 hours at RT followed by 3 washes in TBST. The antibody was eluted from the filter by soaking each filter in 25 ml of 1M acetic acid for 20 minutes. The antibody/acetic acid solution for each of the triplicate samples was pooled and 2 drops of a saturated phenol red solution was added. The solution was neutralized by the addition of an aqueous solution saturated with Tris-HCl and 0.03% BSA was added. The solution was dialyzed against two changes of 1×TBS at 4° C. overnight. The purified antibody solution was collected from the dialysis membrane and a "pinch" of BSA was added. The solution was frozen at −20° C. until needed.

Mini-western blots of purified kalinin were made and exposed to purified antibody from each of the clones for 60-hours at 4° C. Blots were then washed three times in TBST for 15 minutes each. Secondary HRP conjugated antibody was used to illuminate the particular band of kalinin chain corresponding to the clone.

Northern blots were performed as follows. Poly A+RNA was isolated from cell culture of 2 T165 flasks of 70–80% confluent squamous carcinoma cells using Invitrogen's Fast Track RNA isolation systems and exactly following the manufacturer's recommendations. The final RNA pellet was resuspended in 50 ml elution buffer. Twenty mb of Poly A+RNA was used for the gel and subsequent blot using the procedure outlined by Fourney et al. Clone Kal5-5 was radioactively labeled with the Amersham Random labeling system. The blot was placed against X-ray film for 2 hours at −80° C.

3' Rapid Amplification of cDNA Ends (RACE) was performed as follows. A 3' RACE kit was purchased from GIBCO BRL and 1 mg poly A+RNA in 13 ml DEPC-treated water was made into cDNA by reverse transcriptase according to manufacturer's recommendations. The first strand DNA was amplified by PCR following the manufacturer's protocol using the provided antisense poly (T) primer called AP and a specific sense primer for the kalinin B1 chain called D92 (GCT TCA ATG GTC TCC TTA CTA TGT A) (SEQ ID NO: 15).

The Laminin B1k Chain Encodes a Distinct Laminin-like Polypeptide

Analysis of the sequence showed that the first possible translated methionine (first amino acid residue, FIG. 2) is followed by a stretch of hydrophobic amino acid residues which are typical for a signal peptide. From the formula for a signal peptide (von Heijne, 1983 and 1986), the signal peptide would be cleaved following Ala17. The 17 residue long signal peptide is followed by an open reading frame of 1148 amino acid residues with a deduced molecular weight of 126,464 daltons. There are 3 putative N-linked glycosylation sites having the predicted residue sequence Asn-X-Ser/Thr, 3 potential O-linked glycosylation sites having the predicted cluster of three or more consecutive Ser and Thr residues and 2 potential glycosaminoglycan attachment consensus sequences, Ser-Gly-X-Gly. In addition there are 120 nucleotides of 5' untranslated sequences and 315 nucleotides of 3' untranslated sequences for a total of 3931 bases. Northern blot analysis showed a single message of 4.0-kb when probed with the cDNA clone Kal5-5.

Protein Sequencing was performed generally as according to Aebersold et al., 1987. Kalinin purified from amnion (Marinkovich et al., 1992a) was run on a polyacrylamide gel in the presence of 2-mercaptoethanol and blotted on a nitrocellulose membrane (Biorad). The 140-kD band was excised and digested by the protease Lys-C. The digested product was separated by HPLC and one fragment was sequenced on an Applied Biosystem sequencer. Computer analysis of the mature polypeptide demonstrated that the laminin B1k chain is most similar to the human laminin B1chain (LamB1E). A comparison of the laminin B1k polypeptide to this chain is presented in FIG. 3.

Pyroglutamate aminopeptidase reaction was performed generally as according to Andrews et al., 1991. Briefly, kalinin purified from amnion was run on a polyacrylamide gel in presence of 2-mercaptoethanol and blotted on a PVDF membrane in 25 mM Tris, 192 mM glycine, 0.05% SDS and 10% methanol for 4 hours. The 140-kD band was excised, blocked in PVP-40 in 0.1M acetic acid at 37° C. for 30 minutes, washed ten times in water and digested by pyroglutamate aminopeptidase (Boehringer Mannheim) (62.5 mg/mg of protein in 50 mM sodium phosphate, 10 mM EDTA, SmM DTT, 5% glycerol, pH 8.0) for 12 hours at 4° C. An additional 62.5 mg of pyroglutamate aminopeptidase/ mg of protein was added and digestion was done for 12 hours at 37° C. The blot was washed ten times in water, dried under vacuum and subjected to sequencing on an Applied Biosystem sequencer.

Domain Structure of the Laminin B1k Chain

Since the laminin B1k chain has similarity to the laminin B1e chain, its domains were assigned numbers according to their similarity to the comparable domains in laminin (FIG. 4A). Some of the laminin B1e chain domains are missing in the laminin B1k chain and those that remain are all truncated in comparison to the laminin B1e chain. Specifically, the carboxy-terminal ⅓ of domain V, all of domain IV, and the amino-terminal ⅔ of domain III are missing in the laminin B1k chain. FIG. 4A shows a comparison of the domain sizes and percent identity for the various domains of the laminin B1e and laminin B1k chains. The most amino-terminal domain, domain VI (residues 1–231), is a 231-amino acid residue region containing 9 cystine residues. This domain is likely to form a globular structure similar to domain VI in the laminin B1e chain. Domain III/V (residues 232–559) contains six cysteine-rich EGF modules with three of them similar to comparable modules in domain III (EGF 1, 2, and 3) and three of them similar to comparable modules in domain V (EGF 11, 12, 13) of the laminin B1e chain. The laminin B1k chain has no globular domain IV as is found the in the laminin B1e chain. Domain II (residues 560–766), as in the laminin B1e chain, begins with two closely spaced cysteins and is predicted to be an α-helical domain containing heptad repeats typical for coiled-coil proteins. Domain I (residues 798–1148) also contains heptad repeats typical for coiled-coil proteins. Just as in laminin B1e, this domain contains a single cysteine residue one residue away from the carobxyl-terminal end. Also similar to the laminin B1e chain is a cysteine-rich (6 cysteine residues) a domain that interrupts the helical structures of domains I and II.

Since domain VI is the only globular domain retained by the B1k chain, and since the homologous domain in laminin and s-laminin are believed to mediate self-assembly, the sequences of domain VI for B1k, B1e and B1s were compared (FIG. 5). The amino acid identity of domain VI for B1e and B1s shows 70% sequence conservation (FIG. 5). The number and location of cysteinyl residues is identical. Comparisons of the B1k sequence with these two chains shows 49.8% overall sequence identity. As shown in FIG. 5, B1e and B1s contain several regions within domain VI where the sequence identity is above average. Three of these regions share considerably less than average sequence identity with the B1k chain (FIG. 5, underlined). The B1k chain contains an additional cysteine at amino acid residue number 50 (FIG. 5, arrow). This region is also highly divergent from the B1e and B1s chains with an 18% amino acid residue identity to the B1e chain (excluding the obligatory cysteine) whereas, the same region is 70% identical between B1e and B1s. These comparisons suggest that B1k shares an overall structural similarity with B1e and B1s, but the chains are likely to be functionally divergent.

The Laminin B1k Chain is a Truncated Chain

As described above, overlapping cDNA clones encoding the entire 140-kD laminin B1k chain were characterized. The 3.9-kb sequenced corresponds well with the 4.0-kb message size predicted by northern blot analysis. 3' and 5' RACE procedures and were not able to extend the sequence further on either end.

The identity of the cDNAs were confirmed by sequencing a 19-residue long tryptic peptide from the purified 140-kD laminin B1k chain (double-underlined in FIG. 2). Additional protein sequencing of the amino-terminal end of the polypeptide chain confirmed that the end was blocked and therefore most likely began with the residue Gln. After unblocking the end we determined the partial sequence Q-A-C-X-R (X is an indeterminate residue) which corresponds well with our predicted signal peptide cleavage site (start of domain VI, FIG. 2).

The estimated protein size from the cDNAs is 126,464 daltons. This is in contrast to protein data which predicts a protein of about 140,000 daltons. The most likely explanation for this discrepancy is that the chain is glycosylated. There are three potential N-linked glycosylation sites which are underlined in FIG. 2. There are two potential glycosaminoglycan attachment sites marked with stars and three potential N-linked glycosylation sites marked by triangle in FIG. 2. It is interesting to note that the three potential O-linked glycosylation sites are all located in the amino-terminal globular domain, domain VI, which rotary shadowed images predicts to project from the long arm, an ideal position to interact with other molecules such as carbohydrates. In addition, one N-linked glycosylation site is present in the α domain which may extend away from the long arm of the chain and interact with other molecules. The function of the α domain is not known.

The Laminin B1k Chain is Similar to the Laminin B1e and Laminin B1s Chains

FIG. 7 shows a comparison of our cDNA sequence to the B1 and B2 chains of laminin (LAMB1E and LAMB2E), the B2 chain of kalinin (LAMB2T) and the B1 chain of s-laminin (LAMB1S). Since the kalinin B1 chain is clearly related to these other laminin subunits, the convention of Engel et al., 1991 was followed and the Kalinin B1 chain will be named Laminin B1k. As is apparent from FIG. 7, the human laminin B1k chain is most similar to the human laminin B1e (34.1% identity) and rat laminin B1s (37.1% identity) chains. Initially it seemed possible that the laminin B1k chain might be the human equivalent of the laminin B1s chain since the amino acid residue identity was high when considering comparing two different species. There are two pieces of evidence that show that the laminin B1k chain is distinct from the laminin B1s chain. The first is the size of the laminin B1k chain polypeptide which was previously reported to be 140-kD. The laminin B1s chain in rat is about 190-kD which is only slightly smaller than the 200-kD laminin B1e chain. Since there is good conservation of protein size between species (from human to drosophila) for all three of the laminin chains (Laminin Ae, B1e, and B2e), one expects the same will hold true between species for the laminin B1s chain as well and it is predicted that this chain will be 190–200-kD in size. Additional evidence that the laminin B1k chain is distinct from the laminin B1s chain is the fact that a human tryptic peptide sequence was found that is not found in the laminin B1k chain, but has 95.8% identity to the rat laminin B1s chain.

Since the human sequence of the laminin B1s chain is not available, the B1k sequence was compared to the most well described similar molecule, the laminin B1e chain. The major difference between the laminin B1e and laminin B1k chains is their size. The laminin B1k chain has a truncated structure and, therefore, a lower molecular mass than the 200-kD laminin B1e chain. This smaller size is mainly due to the absence of the globular domain which corresponds to domain IV in the laminin B1e chain and to the fact that the corresponding domains III and V are fused into a single domain that is about half the size of the two domain together. There may also be differences in glycosylation between the two polypeptides.

Figure 4:
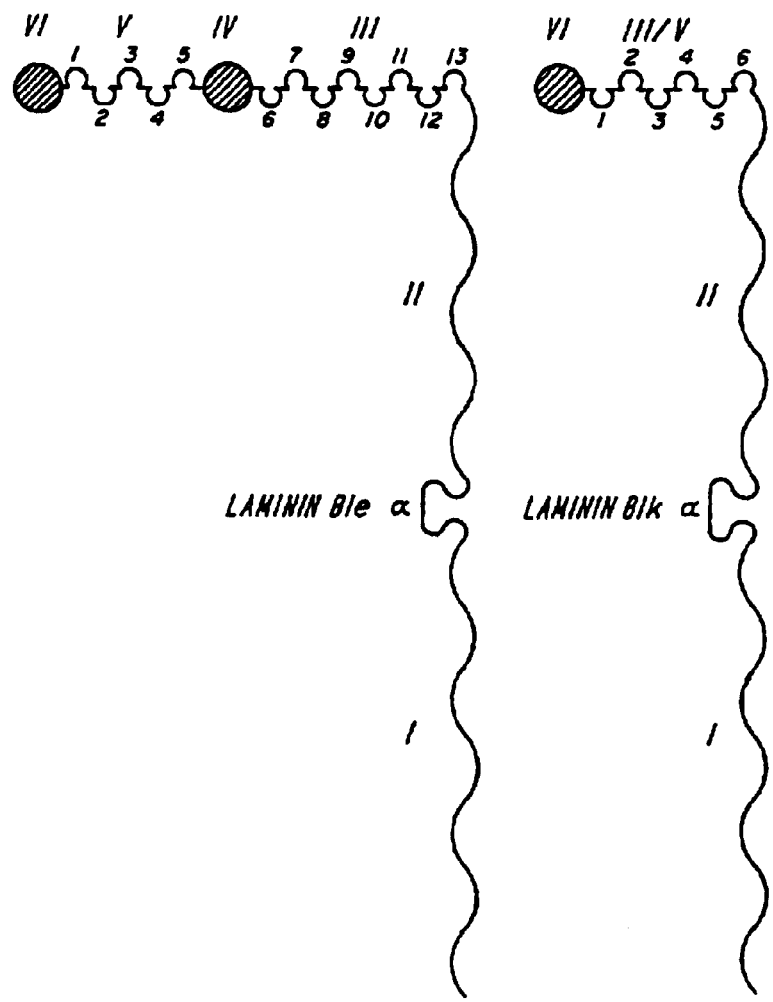
FIG. 4 is: A) a comparison of the domain sizes and percent identity for the various domains of the laminin B1e and laminin B1k chains; and B) a depiction of the numbering scheme for the laminin B1k domains. The domains are numbered according to their similarity to the comparable domains in the laminin B1e chain. Some of the laminin B1e chain domains are missing in the laminin B1k chain and those that remain are truncated in comparison to the laminin B1e chain.

As was found for the laminin B2t chain, the short arms of laminin B1k and laminin B1e have the greatest sequence homology than the long arms (FIG. 4, upper panel: compare domains III–VI, 40–50% identity, to domains I–II, 20–30% identity).

Domain Structure of the Short Arm of the Laminin B1k Chain

The greatest functional significance of the short arm is found in the amino-terminal domain VI. In laminin B1e, domain VI has been reported to aid in the self-assembly of the laminin molecules in vitro. The presence of this domain in the laminin B1k chain suggests that this domain could help to organize the extracellular matrix by associating with either other kalinin or laminin molecules. Since this domain is missing in laminin B2t, if the laminin protein associates with other molecules, then this domain is especially crucial in laminin B1k. One possible ligand for this domain is the recently described K-laminin molecule which contains the laminin B1e and B2e chains and a novel A chain. A second candidate for the interaction is type IV collagen which has been reported to bind to the short arms of the laminin B chains.

The comparison of the B1k sequence to B1e and B1s within the VI domain are particularly interesting. The highly divergent amino acid residue identity in certain areas (FIG. 5, underlined) strongly suggests that domain VI of B1k is functionally different from the other known laminin B1 chains. B1k domain VI also contains an odd number of cysteine residues (FIG. 6, arrow), suggesting that one of these is unpaired and available to stabilize interactions of domain VI with another entity. These observations support the hypothesis that kalinin is unlikely to self-assemble through interactions of the VI domains, but rather, the VI domain specifically interacts with the A chain of K-laminin. In tissues, kalinin is disulfide bonded to K-laminin, but not to other laminins that do not contain the K-laminin A chain. Rotary-shadowed images of the adduct suggest that the short arm region of kalinin associates at the crotch of the K-laminin short arms. Since the B1k chain is the only kalinin chain that remains unprocessed in the mature kalinin molecule, the association with K-laminin appears to be mediated by the B1k chain. The significant diversion in sequence homology between the VI domains of B1k versus B1e and B1s, and the presence of a potentially unpaired cysteine residue are consistent with the concept that the B1k VI domain binds the short arm of the K-laminin A chain enabling alignment of an unpaired cysteine in each molecule and subsequent disulfide bond formation.

Domain IV is missing in the laminin B1k chain and while no functions have been reported for the comparable domain in the laminin B1e chain, some investigators reported small peptide sequences in this area can bind to heparin. Since the entire domain is absent in kalinin these sequences are missing.

Two cell-surface binding peptide sequences (PDSGR and YIGSR) have been reported in the EGF repeat number 9 in domain III of the laminin B1e chain. These peptide sequences are not present since the EGF repeats numbered 6–10 are all missing in domain m of the laminin B1k chain.

Domain Structure of the Long Arm of the Kalinin B1 Chain

The long arm of the laminin B1k chain contains numerous heptad-repeats similar to those found in the two B chains of laminin. The laminin B1e and B2e chains have been found to associate with one another and are in fact disulfide-bonded. Clearly the three chains of kalinin are disulfide-bonded since they can only be separated by gel electrophoresis only after reduction by β-mercaptoethanol. The 155-kD kalinin chain is known to correspond to the previously reported truncated laminin B2t chain by the cDNAs discussed herein as well as to sequenced tryptic peptides (FIG. 7). The laminin B1k chain appears to interact with the laminin B2t chain by forming an α-helix as is found between the laminin B1e and B2e chains and in fact computer analysis predicts that laminin B1k can form an α-helical coiled-coil structure just as laminin B1e. The laminin B1k and the laminin B2t chain each have a single cysteine in their carboxy-terminal regions that are candidates for disulfide-bonding. The laminin B1k chain also has the short cysteine-rich α domain that divides domains I and II and is predicted to stick out from the long-arm and perform as yet unknown functions.

Finally, adhesion of ciliary ganglion neurons has been attributed to the specific sequence LRE in the laminin B1s chain. This sequence is not found in the laminin B1k chain and this function would therefore be missing.

Other Embodiments

Nucleic acid encoding all or part of the B1k chain can be used to transform cells. For example, the B1k gene, e.g., a mis-expressing or mutant form of the B1k gene, e.g., a deletion, or DNA encoding a B1k chain can be used to transform a cell and to produce a cell in which the cell's genomic B1k gene has been replaced by the transformed gene, producing, e.g., a cell deleted for the B1k gene. Such cells can be used with cells capable of being grown in culture, e.g., cultured stem cells, to investigate the function of the B1k gene.

Analogously, nucleic acid encoding all or part of the B1k gene, e.g., a mis-expressing or mutant form of the gene, e.g., a deletion, can be used to transform a cell which subsequently gives rise to a transgenic animal. This approach can be used to create, e.g., a transgenic animal in which the B1k gene is, e.g., inactivated, e.g., by a deletion. Homozygous transgenic animals can be made by crosses between the offspring of a founder transgenic animal. Cell or tissue cultures can be derived from a transgenic animal and the in vivo effects of the laminin B1k chain can subsequently be studied.

The invention includes any fragment of B1k, or any recombinantly produced B1k or fragment thereof which is substantially homologous to a B1k protein, e.g., the B1k protein shown in FIG. 2, or other isoforms. Also included are: allelic variations; natural mutants; induced mutants, e.g., in vitro deletions; proteins encoded by DNA that hybridizes under high or low (e.g., washing at 2×SSC at 40° C. with a probe length of at least 40 nucleotides) stringency conditions to a nucleic acid naturally occurring (for other definitions of high and low stringency see Current Protocols in Molecular Biology, John Wiley & Sons, New York, 1989, 6.3.1–6.3.6, hereby incorporated by reference); and polypeptides or proteins specifically bound by antisera to a B1k protein, especially by antisera to the active site or binding domain of a B1k protein. The term also includes chimeric polypeptides that include a B1k protein.

DNA and peptide sequences of the invention can be, e.g., mouse, primate, e.g., human, or non-naturally occurring sequences.

The invention also includes any biologically active fragment or analog of a B1k protein. By "biologically active" is meant possessing any in vivo or in vitro activity which is characteristic of B1k, e.g., B1k activity as described above. Because the B1k protein exhibits a range of physiological properties and because such properties may be attributable to different portions of the B1k protein molecule, a useful B1k protein fragment or B1k protein analog is one which exhibits a biological activity in any one (or more) of a variety of B1k protein assays, for example, the ability to bind the laminin Ak chain, as described above. A B1k protein fragment or analog possesses, most preferably 90%, preferably 40%, or at least 10%, of the activity of a naturally occurring B1k isoform, e.g., of the B1k protein shown in FIG. 2, in any in vivo or in vitro B1k assay.

Preferred analogs include B1k peptides or recombinant B1k proteins or peptides (or biologically active fragments thereof) whose sequences differ from the wild-type sequence by one or more conservative amino acid substitutions or by one or more non-conservative amino acid substitutions, deletions, or insertions which do not abolish biological activity. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Other conservative substitutions can be taken from the table below.

| CONSERVATIVE AMINO ACID REPLACEMENTS | | |
|---|---|---|
| For Amino Acid | Code | Replace with any of |
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, β-Ala Acp |
| Isoleucine | I | D-Ile, Val, D-Val, Leu, D-Leu, Met, D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-I-thioazolidine-4-carboxylic acid, D- or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-I, eu, Ile, D-Ile, Met, D-Met |

Other useful modifications include those which increase peptide stability; such analogs may contain, for example, one or more non-peptide bonds (which replace peptide bonds) or D-amino acids in the peptide sequence.

Analogs can differ from a naturally occurring B1k protein in amino acid sequence or can modified in ways that do not affect sequence, or both. Analogs of the invention will generally exhibit at least 70%, more preferably 80%, more preferably 90%, and most preferably 95% or even, 99%, homology with a segment of 20 amino acid residues, preferably more than 40 amino acid residues or more preferably the entire sequence of naturally occurring B1k protein sequence.

Alterations in primary sequence include genetic variations, both natural and induced. Also included are analogs that include residues other than naturally occurring L-amino acids, e.g., D-amino acids or non-naturally occurring or synthetic amino acids, e.g., β or γ amino acids. Alternatively, increased stability may be conferred by cyclizing the peptide molecule.

Nonsequence modification include in vivo or in vitro chemical derivatization or polypeptides, e.g., acetylation, methylation, phosphorylation, carboxylation, or glycosylation; glycosylation can be modified, e.g., by modifying the glycosylation patterns of a polypeptide during its synthesis and processing or in further processing steps, e.g., by exposing the polypeptide to glycosylation-affecting enzymes derived from cells that normally provide such processing, e.g., mammalian glycosylation enzymes; phosphorylation can be modified by exposing the polypeptide to phosphorylation-altering enzymes, e.g., kinases or phosphatases.

Fragments of B1k proteins or peptides can be made by methods known to those skilled in the art, e.g., by expressing B1k DNA which has been manipulated in vitro to encode the desired fragment; e.g., by restriction digestion or other manipulation of a B1k DNA e.g., the sequence in FIG. 2. Analogs can be made by methods known to those skilled in the art, e.g., by in vitro DNA sequence modifications of the sequence of a B1k DNA e.g., the sequence in FIG. 2. For example, in vitro mutagenesis can be used to convert the DNA sequence of FIG. 2 into a sequence which encodes an analog in which one or more amino acid residues has undergone a replacement, e.g., a conservative replacement as described in the table of conservative amino acid substitutions provided herein. Fragments or analogs can be tested by methods known to those skilled in the art for the presence of B1k activity.

Also included are B1k protein polypeptides containing residues that are not required for biological activity of the peptide, such as residues that are not required for the biological activity of the polypeptide, or that result from alternative mRNA splicing or alternative protein processing events.

The invention also includes nucleic acids encoding the polypeptides of the invention.

In order to obtain a B1k protein, or fragment thereof, one can insert B1k-encoding DNA into an expression vector, introduce the vector into a cell suitable for expression of the desired protein, and recover and purify the desired protein by prior art methods. Antibodies to B1k proteins can be made by immunizing an animal, e.g., a rabbit or mouse, and recovering anti-B1k antibodies by prior art methods.

Other embodiments are within the following claims.

SEQUENCE LISTING

```
<160> NUMBER OF SEQ ID NOS: 14

<210> SEQ ID NO 1
<211> LENGTH: 3931
<212> TYPE: DNA
<213> ORGANISM: Homo sapiens
<220> FEATURE:
<221> NAME/KEY: CDS
<222> LOCATION: (122)..(3616)
<220> FEATURE:
<221> NAME/KEY: mat_peptide
<222> LOCATION: (173)..(3616)

<400> SEQUENCE: 1
gggcgtggag gaggactgta tctctggatg cctggggcct ggtttcaggg cctgatttat      60
tcctcttcct gggagctcac tcaggaaagg tcctttctgg ggatcacccc attggctgaa     120 g atg aga cca ttc ttc ctc ttg tgt ttt gcc ctg cct ggc ctc ctg cat     169
  Met Arg Pro Phe Phe Leu Leu Cys Phe Ala Leu Pro Gly Leu Leu His
      -15                 -10                 -5
gcc caa caa gcc tgc tcc cgt ggg gcc tgc tat cca cct gtt ggg gac       217
Ala Gln Gln Ala Cys Ser Arg Gly Ala Cys Tyr Pro Pro Val Gly Asp
 -1   1               5                  10                  15 ctg ctt gtt ggg agg acc cgg ttt ctc cga gct tca tct acc tgt gga       265
Leu Leu Val Gly Arg Thr Arg Phe Leu Arg Ala Ser Ser Thr Cys Gly
                20                  25                  30 ctg acc aag cct gag acc tac tgc acc cag tat ggc gag tgg cag atg       313
Leu Thr Lys Pro Glu Thr Tyr Cys Thr Gln Tyr Gly Glu Trp Gln Met
            35                  40                  45 aaa tgc tgc aag tgt gac tcc agg cag cct cac aac tac tac agt cac       361
Lys Cys Cys Lys Cys Asp Ser Arg Gln Pro His Asn Tyr Tyr Ser His
        50                  55                  60
```

-continued

```
cga gta gag aat gtg gct tca tcc tcc ggc ccc atg cgc tgg tgg cag      409
Arg Val Glu Asn Val Ala Ser Ser Ser Gly Pro Met Arg Trp Trp Gln
     65                  70                  75 tcc cag aat gat gtg aac cct gtc tct ctg cag ctg gac ctg gac agg      457
Ser Gln Asn Asp Val Asn Pro Val Ser Leu Gln Leu Asp Leu Asp Arg
 80                  85                  90                  95 aga ttc cag ctt caa gaa gtc atg atg gag ttc cca ggg gcc cat gct      505
Arg Phe Gln Leu Gln Glu Val Met Met Glu Phe Pro Gly Ala His Ala
                100                 105                 110 gcc ggc atg ctg att gag cgc tcc tca gac ttc ggt aag acc tgg cga      553
Ala Gly Met Leu Ile Glu Arg Ser Ser Asp Phe Gly Lys Thr Trp Arg
            115                 120                 125 gtg tac cag tac ctg gct gcc gac tgc acc tcc acc ttc cct cgg gtc      601
Val Tyr Gln Tyr Leu Ala Ala Asp Cys Thr Ser Thr Phe Pro Arg Val
        130                 135                 140 cgc cag ggt cgg cct cag agc tgg cag gat gtt cgg tgc cag tcc ctg      649
Arg Gln Gly Arg Pro Gln Ser Trp Gln Asp Val Arg Cys Gln Ser Leu
    145                 150                 155 cct cag agg cct aat gca cgc cta aat ggg ggg aag gtc caa ctt aac      697
Pro Gln Arg Pro Asn Ala Arg Leu Asn Gly Gly Lys Val Gln Leu Asn
160                 165                 170                 175 ctt atg gat tta gtg tct ggg att cca gca act caa agt caa aaa att      745
Leu Met Asp Leu Val Ser Gly Ile Pro Ala Thr Gln Ser Gln Lys Ile
                180                 185                 190 caa gag gtg ggg gag atc aca aac ttg aga gtc aat ttc acc agg ctg      793
Gln Glu Val Gly Glu Ile Thr Asn Leu Arg Val Asn Phe Thr Arg Leu
            195                 200                 205 gcc cct gtg ccc aaa ctg gac cac cct ccc agc gcc tac tat gct gtg      841
Ala Pro Val Pro Lys Leu Asp His Pro Pro Ser Ala Tyr Tyr Ala Val
        210                 215                 220 tcc cag ctc cgt ctg cag ggg agc tgc ttc tgt cac ggc cat gct gat      889
Ser Gln Leu Arg Leu Gln Gly Ser Cys Phe Cys His Gly His Ala Asp
    225                 230                 235 cgc tgc gca ccc aag cct ggg gcc tct gca ggc tcc acc gct gtg cag      937
Arg Cys Ala Pro Lys Pro Gly Ala Ser Ala Gly Ser Thr Ala Val Gln
240                 245                 250                 255 gtc cac gat gtc tgc gtc tgc cag cac aac act gcc ggc cca aat tgt      985
Val His Asp Val Cys Val Cys Gln His Asn Thr Ala Gly Pro Asn Cys
                260                 265                 270 gag cgc tgt gca ccc ttc tac aac aac cgg ccc tgg aga ccg gcg gag     1033
Glu Arg Cys Ala Pro Phe Tyr Asn Asn Arg Pro Trp Arg Pro Ala Glu
            275                 280                 285 ggc cag gac gcc cat gaa tgc caa agg tgc gac tgc aat ggg cac tca     1081
Gly Gln Asp Ala His Glu Cys Gln Arg Cys Asp Cys Asn Gly His Ser
        290                 295                 300 gag aac tgt cac ttt gac ccc gct gtg ttt gcc gcc agc cag ggg gca     1129
Glu Asn Cys His Phe Asp Pro Ala Val Phe Ala Ala Ser Gln Gly Ala
    305                 310                 315 tat gga ggt gtg tgt gac aat tgc cgg gac cac acc gaa ggc aag aac     1177
Tyr Gly Gly Val Cys Asp Asn Cys Arg Asp His Thr Glu Gly Lys Asn
320                 325                 330                 335 tgt gag cgg tgt cag ctg cac tat ttc cgg aac cgc cgc ccg gga gct     1225
Cys Glu Arg Cys Gln Leu His Tyr Phe Arg Asn Arg Arg Pro Gly Ala
                340                 345                 350 tcc att cag gag acc tgc atc tcc tgc gag tgt gat ccg gat ggg cag     1273
Ser Ile Gln Glu Thr Cys Ile Ser Cys Glu Cys Asp Pro Asp Gly Gln
            355                 360                 365 tgg gca ggg gct ccc tgt gac cca gtg acc ggg cag tgt gtg tgc aag     1321
Trp Ala Gly Ala Pro Cys Asp Pro Val Thr Gly Gln Cys Val Cys Lys
```

```
                      370                 375                 380
gag cat gtg cag gga gag cgc tgt gac cta tgc aag ccg ggc ttc act      1369
Glu His Val Gln Gly Glu Arg Cys Asp Leu Cys Lys Pro Gly Phe Thr
    385                 390                 395 gga ctc acc tac gcc aac ccg cag ggc tgc cac cgc tgt gac tgc aac      1417
Gly Leu Thr Tyr Ala Asn Pro Gln Gly Cys His Arg Cys Asp Cys Asn
400                 405                 410                 415 atc ctg ccc tcc cgg aga ctg ccg tgt gac gag gag agt ggg cgc tgc      1465
Ile Leu Pro Ser Arg Arg Leu Pro Cys Asp Glu Glu Ser Gly Arg Cys
                420                 425                 430 ctt tgt ctg ccc aac gta ggt ggt ccc aaa tgt gac cag tgt gct ccc      1513
Leu Cys Leu Pro Asn Val Gly Gly Pro Lys Cys Asp Gln Cys Ala Pro
            435                 440                 445 tac cac tgg aag ctg gcc agt ggc cag ggc tgt gaa ccg tgt gcc tgc      1561
Tyr His Trp Lys Leu Ala Ser Gly Gln Gly Cys Glu Pro Cys Ala Cys
        450                 455                 460 gac ccg cac aac tcc ctc agc cca cag tgc aac cag ttc aca ggg cag      1609
Asp Pro His Asn Ser Leu Ser Pro Gln Cys Asn Gln Phe Thr Gly Gln
465                 470                 475 tgc ccc tgt cgg gaa ggc ttt ggt ggc ctg atg tgc agc gct gca gcc      1657
Cys Pro Cys Arg Glu Gly Phe Gly Gly Leu Met Cys Ser Ala Ala Ala
480                 485                 490                 495 atc cgc cag tgt cca gac cgg acc tat gga gac gtg gcc aca gga tgc      1705
Ile Arg Gln Cys Pro Asp Arg Thr Tyr Gly Asp Val Ala Thr Gly Cys
                500                 505                 510 cga gcc tgt gac tgt gat ttc cgg gga aca gag ggc ccg ggc tgc gac      1753
Arg Ala Cys Asp Cys Asp Phe Arg Gly Thr Glu Gly Pro Gly Cys Asp
            515                 520                 525 aag gca tca ggc gtg ctc tgc cgc cct ggc ttg acc ggg ccc cgc tgt      1801
Lys Ala Ser Gly Val Leu Cys Arg Pro Gly Leu Thr Gly Pro Arg Cys
        530                 535                 540 gac cag tgc cag cga ggc tac tgc aat cgc tac ccg gtg tgc gtg gcc      1849
Asp Gln Cys Gln Arg Gly Tyr Cys Asn Arg Tyr Pro Val Cys Val Ala
545                 550                 555 tgc cac cct tgc ttc cag acc tat gat gcg gac ctc cgg gag cag gcc      1897
Cys His Pro Cys Phe Gln Thr Tyr Asp Ala Asp Leu Arg Glu Gln Ala
560                 565                 570                 575 ctg cgc ttt ggt aga ctc ccg aat gcc acc gcc agc ctg tgg tca ggg      1945
Leu Arg Phe Gly Arg Leu Pro Asn Ala Thr Ala Ser Leu Trp Ser Gly
                580                 585                 590 cct ggg ctg gag gac cgt ggc ctg gcc tcc cgg atc cta gat gca aag      1993
Pro Gly Leu Glu Asp Arg Gly Leu Ala Ser Arg Ile Leu Asp Ala Lys
            595                 600                 605 agt aag att gag cag atc cga gca gtt ctc agc agc ccc gca gtc aca      2041
Ser Lys Ile Glu Gln Ile Arg Ala Val Leu Ser Ser Pro Ala Val Thr
        610                 615                 620 gag cag gag gtg gct cag gtg gcc agt gcc atc ctc tcc ctc agg cga      2089
Glu Gln Glu Val Ala Gln Val Ala Ser Ala Ile Leu Ser Leu Arg Arg
625                 630                 635 act ctc cag ggc ctg cag ctg gat ctg ccc ctg gag gag gag acg ttg      2137
Thr Leu Gln Gly Leu Gln Leu Asp Leu Pro Leu Glu Glu Glu Thr Leu
640                 645                 650                 655 tcc ctt ccg aga gac ctg gag agt ctt gac aga agc ttc aat ggt ctc      2185
Ser Leu Pro Arg Asp Leu Glu Ser Leu Asp Arg Ser Phe Asn Gly Leu
                660                 665                 670 ctt act atg tat cag agg aag agg gag cag ttt gaa aaa ata agc agt      2233
Leu Thr Met Tyr Gln Arg Lys Arg Glu Gln Phe Glu Lys Ile Ser Ser
            675                 680                 685 gct gat cct tca gga gcc ttc cgg atg ctg agc aca gcc tac gag cag      2281
Ala Asp Pro Ser Gly Ala Phe Arg Met Leu Ser Thr Ala Tyr Glu Gln
```

```
                Ala Asp Pro Ser Gly Ala Phe Arg Met Leu Ser Thr Ala Tyr Glu Gln
                            690                 695                 700 tca gcc cag gct gct cag cag gtc tcc gac agc tcg cgc ctt ttg gac          2329
Ser Ala Gln Ala Ala Gln Gln Val Ser Asp Ser Ser Arg Leu Leu Asp
705                 710                 715 cag ctc agg gac agc cgg aga gag gca gag agg ctg gtg cgg cag gcg          2377
Gln Leu Arg Asp Ser Arg Arg Glu Ala Glu Arg Leu Val Arg Gln Ala
720                 725                 730                 735 gga gga gga gga ggc acc ggc agc ccc aag ctt gtg gcc ctg agg ttg          2425
Gly Gly Gly Gly Gly Thr Gly Ser Pro Lys Leu Val Ala Leu Arg Leu
                740                 745                 750 gag atg tct tcg ttg cct gac ctg aca ccc acc ttc aac aag ctc tgt          2473
Glu Met Ser Ser Leu Pro Asp Leu Thr Pro Thr Phe Asn Lys Leu Cys
            755                 760                 765 ggc aac tcc agg cag atg gct tgc acc cca ata tca tgc cct ggt gag          2521
Gly Asn Ser Arg Gln Met Ala Cys Thr Pro Ile Ser Cys Pro Gly Glu
        770                 775                 780 cta tgt ccc caa gac aat ggc aca gcc tgt gcg tcc cgc tgc agg ggt          2569
Leu Cys Pro Gln Asp Asn Gly Thr Ala Cys Ala Ser Arg Cys Arg Gly
    785                 790                 795 gtc ctt ccc agg gcc ggt ggg gcc ttc ttg atg gcg ggg cag gtg gct          2617
Val Leu Pro Arg Ala Gly Gly Ala Phe Leu Met Ala Gly Gln Val Ala
800                 805                 810                 815 gag cag ctg cgg gct tca atg cca gct cca gcg acc agg cag atg att          2665
Glu Gln Leu Arg Ala Ser Met Pro Ala Pro Ala Thr Arg Gln Met Ile
                820                 825                 830 agg gca gcc gag gaa tct gcc tca cag att caa tcc agt gcc cag cgc          2713
Arg Ala Ala Glu Glu Ser Ala Ser Gln Ile Gln Ser Ser Ala Gln Arg
            835                 840                 845 ttg gag acc cag gtg agc gcc agc cgc tcc cag atg gag gaa gat gtc          2761
Leu Glu Thr Gln Val Ser Ala Ser Arg Ser Gln Met Glu Glu Asp Val
        850                 855                 860 aga cgc aca cgg ctc cta atc cag cag gtc cgg gac ttc cta aca gac          2809
Arg Arg Thr Arg Leu Leu Ile Gln Gln Val Arg Asp Phe Leu Thr Asp
    865                 870                 875 ccc gac act gat gca gcc act atc cag gag gtc agg cga gcc gtg ctg          2857
Pro Asp Thr Asp Ala Ala Thr Ile Gln Glu Val Arg Arg Ala Val Leu
880                 885                 890                 895 gcc ctg tgg ctg ccc aca gac tca gct act gtt ctg cag aag atg aat          2905
Ala Leu Trp Leu Pro Thr Asp Ser Ala Thr Val Leu Gln Lys Met Asn
                900                 905                 910 gag atc cag gcc att gca gcc agg ctc ccc aac gtg gac ttg gtg ctg          2953
Glu Ile Gln Ala Ile Ala Ala Arg Leu Pro Asn Val Asp Leu Val Leu
            915                 920                 925 tcc cag acc aag cag gac att ggc ggt gcc cgc cgg ttg cag gct gag          3001
Ser Gln Thr Lys Gln Asp Ile Gly Gly Ala Arg Arg Leu Gln Ala Glu
        930                 935                 940 gct gag gaa gcc agg agc cga gcc cat gca gtg gag ggc cag gtg gag          3049
Ala Glu Glu Ala Arg Ser Arg Ala His Ala Val Glu Gly Gln Val Glu
    945                 950                 955 gat gtg gtt ggg aac ctg cgg cag ggg aca gtg gca ctg cag gaa gct          3097
Asp Val Val Gly Asn Leu Arg Gln Gly Thr Val Ala Leu Gln Glu Ala
960                 965                 970                 975 cag gac acc atg caa ggc acc agc cgg tcc ctt cgg ctt atc cag gac          3145
Gln Asp Thr Met Gln Gly Thr Ser Arg Ser Leu Arg Leu Ile Gln Asp
                980                 985                 990 agg gtt gct gag gtt cag cag gta ctc ggc cag caa aag ctg gtg aca          3193
Arg Val Ala Glu Val Gln Gln Val Leu Gly Gln Gln Lys Leu Val Thr
            995                 1000                1005
```

| | |
|---|---|
| agc atg acc aag cag ctg ggt gac ttc tgg aca cgg atg gag gag ctc<br>Ser Met Thr Lys Gln Leu Gly Asp Phe Trp Thr Arg Met Glu Glu Leu<br>       1010                 1015            1020 | 3241 |
| cgc cac caa gcc cgg cag cag ggg gca gag gca gtc cag gcc cag cag<br>Arg His Gln Ala Arg Gln Gln Gly Ala Glu Ala Val Gln Ala Gln Gln<br>1025                 1030                1035 | 3289 |
| ctt gcg gaa ggt gcc agc gag cag gca ttg agt gcc caa gag gga ttt<br>Leu Ala Glu Gly Ala Ser Glu Gln Ala Leu Ser Ala Gln Glu Gly Phe<br>1040                 1045                1050                1055 | 3337 |
| gag aga ata aaa caa aag tat gct gag ttg aag gac cgg ttg ggt cag<br>Glu Arg Ile Lys Gln Lys Tyr Ala Glu Leu Lys Asp Arg Leu Gly Gln<br>                 1060                 1065            1070 | 3385 |
| agt tcc atg ctg ggt gag cag ggt gcc cgg atc cag agt gtg aag aca<br>Ser Ser Met Leu Gly Glu Gln Gly Ala Arg Ile Gln Ser Val Lys Thr<br>                 1075                 1080            1085 | 3433 |
| gag gca gag gag ctg ttt ggg gag acc atg gag atg atg gac agg atg<br>Glu Ala Glu Glu Leu Phe Gly Glu Thr Met Glu Met Met Asp Arg Met<br>                 1090                 1095            1100 | 3481 |
| aaa gac atg gag ttg gag ctg ctg cgg gca gca ggc cat cat gct gcg<br>Lys Asp Met Glu Leu Glu Leu Leu Arg Ala Ala Gly His His Ala Ala<br>1105                 1110                1115 | 3529 |
| ctc agc gac ctg aca gga ctg gag aag cgt gtg gag cag atc cgt gac<br>Leu Ser Asp Leu Thr Gly Leu Glu Lys Arg Val Glu Gln Ile Arg Asp<br>1120                 1125                1130            1135 | 3577 |
| cac atc aat ggg cgc gtg ctc tac tat gcc acc tgc aag tgatgctaca<br>His Ile Asn Gly Arg Val Leu Tyr Tyr Ala Thr Cys Lys<br>                 1140                 1145 | 3626 |
| cgttccagcc cgttgcccca ctcatctgcg cgctttgctt ttggttgggg ggcagattgg | 3686 |
| gttggaatgc tttccatctc caggagactt tcatgtagcc caaagtacag cctggaccac | 3746 |
| ccctggtgtg agtagctagt aagattaccc tgagctgcag ctgagcctga gccaatggga | 3806 |
| cagttacact tgacagacaa agatggtgga gattggcatg ccattgaaac taagagctct | 3866 |
| caagtcaagg aagctgggct gggcagtatc ccccgccttt agttctccac aaaaaaaaaa | 3926 |
| aaaaa | 3931 |

<210> SEQ ID NO 2
<211> LENGTH: 1165
<212> TYPE: PRT
<213> ORGANISM: Homo sapiens

<400> SEQUENCE: 2

Met Arg Pro Phe Phe Leu Leu Cys Phe Ala Leu Pro Gly Leu Leu His
        -15                  -10                   -5

Ala Gln Gln Ala Cys Ser Arg Gly Ala Cys Tyr Pro Pro Val Gly Asp
 -1  1            5                  10                  15

Leu Leu Val Gly Arg Thr Arg Phe Leu Arg Ala Ser Ser Thr Cys Gly
                20                  25                  30

Leu Thr Lys Pro Glu Thr Tyr Cys Thr Gln Tyr Gly Glu Trp Gln Met
                35                  40                  45

Lys Cys Cys Lys Cys Asp Ser Arg Gln Pro His Asn Tyr Tyr Ser His
                50                  55                  60

Arg Val Glu Asn Val Ala Ser Ser Ser Gly Pro Met Arg Trp Trp Gln
        65                  70                  75

Ser Gln Asn Asp Val Asn Pro Val Ser Leu Gln Leu Asp Leu Asp Arg
80                  85                  90                  95

Arg Phe Gln Leu Gln Glu Val Met Met Glu Phe Pro Gly Ala His Ala
                100                105               110

-continued

```
Ala Gly Met Leu Ile Glu Arg Ser Ser Asp Phe Gly Lys Thr Trp Arg
            115                 120                 125
Val Tyr Gln Tyr Leu Ala Ala Asp Cys Thr Ser Thr Phe Pro Arg Val
            130                 135             140
Arg Gln Gly Arg Pro Gln Ser Trp Gln Asp Val Arg Cys Gln Ser Leu
        145                 150                 155
Pro Gln Arg Pro Asn Ala Arg Leu Asn Gly Gly Lys Val Gln Leu Asn
160                 165                 170                 175
Leu Met Asp Leu Val Ser Gly Ile Pro Ala Thr Gln Ser Gln Lys Ile
                180                 185                 190
Gln Glu Val Gly Glu Ile Thr Asn Leu Arg Val Asn Phe Thr Arg Leu
            195                 200                 205
Ala Pro Val Pro Lys Leu Asp His Pro Ser Ala Tyr Tyr Ala Val
            210                 215                 220
Ser Gln Leu Arg Leu Gln Gly Ser Cys Phe Cys His Gly His Ala Asp
        225                 230                 235
Arg Cys Ala Pro Lys Pro Gly Ala Ser Ala Gly Ser Thr Ala Val Gln
240                 245                 250                 255
Val His Asp Val Cys Val Cys Gln His Asn Thr Ala Gly Pro Asn Cys
                260                 265                 270
Glu Arg Cys Ala Pro Phe Tyr Asn Asn Arg Pro Trp Arg Pro Ala Glu
            275                 280                 285
Gly Gln Asp Ala His Glu Cys Gln Arg Cys Asp Cys Asn Gly His Ser
            290                 295                 300
Glu Asn Cys His Phe Asp Pro Ala Val Phe Ala Ala Ser Gln Gly Ala
        305                 310                 315
Tyr Gly Gly Val Cys Asp Asn Cys Arg Asp His Thr Glu Gly Lys Asn
320                 325                 330                 335
Cys Glu Arg Cys Gln Leu His Tyr Phe Arg Asn Arg Pro Gly Ala
                340                 345                 350
Ser Ile Gln Glu Thr Cys Ile Ser Cys Glu Cys Asp Pro Asp Gly Gln
            355                 360                 365
Trp Ala Gly Ala Pro Cys Asp Pro Val Thr Gly Gln Cys Val Cys Lys
        370                 375                 380
Glu His Val Gln Gly Glu Arg Cys Asp Leu Cys Lys Pro Gly Phe Thr
        385                 390                 395
Gly Leu Thr Tyr Ala Asn Pro Gln Gly Cys His Arg Cys Asp Cys Asn
400                 405                 410                 415
Ile Leu Pro Ser Arg Arg Leu Pro Cys Asp Glu Glu Ser Gly Arg Cys
                420                 425                 430
Leu Cys Leu Pro Asn Val Gly Gly Pro Lys Cys Asp Gln Cys Ala Pro
            435                 440                 445
Tyr His Trp Lys Leu Ala Ser Gly Gln Gly Cys Glu Pro Cys Ala Cys
        450                 455                 460
Asp Pro His Asn Ser Leu Ser Pro Gln Cys Asn Gln Phe Thr Gly Gln
465                 470                 475
Cys Pro Cys Arg Glu Gly Phe Gly Gly Leu Met Cys Ser Ala Ala Ala
480                 485                 490                 495
Ile Arg Gln Cys Pro Asp Arg Thr Tyr Gly Asp Val Ala Thr Gly Cys
                500                 505                 510
Arg Ala Cys Asp Cys Asp Phe Arg Gly Thr Glu Gly Pro Gly Cys Asp
            515                 520                 525
```

-continued

```
Lys Ala Ser Gly Val Leu Cys Arg Pro Gly Leu Thr Gly Pro Arg Cys
        530                 535                 540

Asp Gln Cys Gln Arg Gly Tyr Cys Asn Arg Tyr Pro Val Cys Val Ala
545                 550                 555

Cys His Pro Cys Phe Gln Thr Tyr Asp Ala Asp Leu Arg Glu Gln Ala
560                 565                 570                 575

Leu Arg Phe Gly Arg Leu Pro Asn Ala Thr Ala Ser Leu Trp Ser Gly
                580                 585                 590

Pro Gly Leu Glu Asp Arg Gly Leu Ala Ser Arg Ile Leu Asp Ala Lys
                595                 600                 605

Ser Lys Ile Glu Gln Ile Arg Ala Val Leu Ser Ser Pro Ala Val Thr
        610                 615                 620

Glu Gln Glu Val Ala Gln Val Ala Ser Ala Ile Leu Ser Leu Arg Arg
625                 630                 635

Thr Leu Gln Gly Leu Gln Leu Asp Leu Pro Leu Glu Glu Thr Leu
640                 645                 650                 655

Ser Leu Pro Arg Asp Leu Glu Ser Leu Asp Arg Ser Phe Asn Gly Leu
                660                 665                 670

Leu Thr Met Tyr Gln Arg Lys Arg Glu Gln Phe Glu Lys Ile Ser Ser
            675                 680                 685

Ala Asp Pro Ser Gly Ala Phe Arg Met Leu Ser Thr Ala Tyr Glu Gln
            690                 695                 700

Ser Ala Gln Ala Ala Gln Val Ser Asp Ser Ser Arg Leu Leu Asp
            705                 710                 715

Gln Leu Arg Asp Ser Arg Arg Glu Ala Glu Arg Leu Val Arg Gln Ala
720                 725                 730                 735

Gly Gly Gly Gly Gly Thr Gly Ser Pro Lys Leu Val Ala Leu Arg Leu
                740                 745                 750

Glu Met Ser Ser Leu Pro Asp Leu Thr Pro Thr Phe Asn Lys Leu Cys
            755                 760                 765

Gly Asn Ser Arg Gln Met Ala Cys Thr Pro Ile Ser Cys Pro Gly Glu
        770                 775                 780

Leu Cys Pro Gln Asp Asn Gly Thr Ala Cys Ala Ser Arg Cys Arg Gly
785                 790                 795

Val Leu Pro Arg Ala Gly Gly Ala Phe Leu Met Ala Gly Gln Val Ala
800                 805                 810                 815

Glu Gln Leu Arg Ala Ser Met Pro Ala Pro Ala Thr Arg Gln Met Ile
                820                 825                 830

Arg Ala Ala Glu Glu Ser Ala Ser Gln Ile Gln Ser Ser Ala Gln Arg
                835                 840                 845

Leu Glu Thr Gln Val Ser Ala Ser Arg Ser Gln Met Glu Glu Asp Val
        850                 855                 860

Arg Arg Thr Arg Leu Leu Ile Gln Gln Val Arg Asp Phe Leu Thr Asp
865                 870                 875

Pro Asp Thr Asp Ala Ala Thr Ile Gln Glu Val Arg Arg Ala Val Leu
880                 885                 890                 895

Ala Leu Trp Leu Pro Thr Asp Ser Ala Thr Val Leu Gln Lys Met Asn
                900                 905                 910

Glu Ile Gln Ala Ile Ala Arg Leu Pro Asn Val Asp Leu Val Leu
            915                 920                 925

Ser Gln Thr Lys Gln Asp Ile Gly Gly Ala Arg Arg Leu Gln Ala Glu
        930                 935                 940

Ala Glu Glu Ala Arg Ser Arg Ala His Ala Val Glu Gly Gln Val Glu
```

-continued

```
                945                 950                 955
Asp Val Val Gly Asn Leu Arg Gln Gly Thr Val Ala Leu Gln Glu Ala
960                 965                 970                 975

Gln Asp Thr Met Gln Gly Thr Ser Arg Ser Leu Arg Leu Ile Gln Asp
                980                 985                 990

Arg Val Ala Glu Val Gln Gln Val Leu Gly Gln Gln Lys Leu Val Thr
                995                1000                1005

Ser Met Thr Lys Gln Leu Gly Asp Phe Trp Thr Arg Met Glu Glu Leu
               1010                1015                1020

Arg His Gln Ala Arg Gln Gln Gly Ala Glu Ala Val Gln Ala Gln Gln
               1025                1030                1035

Leu Ala Glu Gly Ala Ser Glu Gln Ala Leu Ser Ala Gln Glu Gly Phe
1040                1045                1050                1055

Glu Arg Ile Lys Gln Lys Tyr Ala Glu Leu Lys Asp Arg Leu Gly Gln
               1060                1065                1070

Ser Ser Met Leu Gly Glu Gln Gly Ala Arg Ile Gln Ser Val Lys Thr
               1075                1080                1085

Glu Ala Glu Glu Leu Phe Gly Glu Thr Met Glu Met Met Asp Arg Met
               1090                1095                1100

Lys Asp Met Glu Leu Glu Leu Leu Arg Ala Ala Gly His His Ala Ala
               1105                1110                1115

Leu Ser Asp Leu Thr Gly Leu Glu Lys Arg Val Glu Gln Ile Arg Asp
1120                1125                1130                1135

His Ile Asn Gly Arg Val Leu Tyr Tyr Ala Thr Cys Lys
               1140                1145
```

```
<210> SEQ ID NO 3
<211> LENGTH: 1147
<212> TYPE: PRT
<213> ORGANISM: Artificial Sequence
<220> FEATURE:
<221> NAME/KEY: DOMAIN
<222> LOCATION: (1)...(231)
<223> OTHER INFORMATION: Laminin B1k chain
<220> FEATURE:
<221> NAME/KEY: DOMAIN
<222> LOCATION: (232)...(411)
<223> OTHER INFORMATION: Laminin B1k chain
<220> FEATURE:
<221> NAME/KEY: DOMAIN
<222> LOCATION: (412)...(765)
<223> OTHER INFORMATION: Laminin B1k chain
<220> FEATURE:
<221> NAME/KEY: DOMAIN
<222> LOCATION: (766)...(1147)
<223> OTHER INFORMATION: Laminin B1k chain

<400> SEQUENCE: 3
```

```
Gln Gln Ala Cys Ser Arg Gly Ala Cys Tyr Pro Pro Val Gly Asp Leu
  1               5                  10                  15

Leu Val Gly Arg Thr Arg Phe Leu Arg Ala Ser Ser Thr Cys Gly Leu
                 20                  25                  30

Thr Lys Pro Glu Thr Tyr Cys Thr Gln Tyr Gly Glu Trp Gln Met Lys
             35                  40                  45

Cys Cys Lys Cys Asp Ser Arg Gln Pro His Asn Tyr Tyr Ser His Arg
         50                  55                  60

Val Glu Asn Val Ala Ser Ser Gly Pro Met Arg Trp Trp Gln Ser
 65                  70                  75                  80

Gln Asn Asp Val Asn Pro Val Ser Leu Gln Leu Asp Leu Asp Arg Arg
                 85                  90                  95
```

-continued

```
Phe Gln Leu Gln Glu Val Met Met Glu Phe Pro Gly Ala His Ala Ala
            100                 105                 110
Gly Met Leu Ile Glu Arg Ser Ser Asp Phe Gly Lys Thr Trp Arg Val
            115                 120                 125
Tyr Gln Tyr Leu Ala Ala Asp Cys Thr Ser Thr Phe Pro Arg Val Arg
            130                 135                 140
Gln Gly Arg Pro Gln Ser Trp Gln Asp Val Arg Cys Gln Ser Leu Pro
145                 150                 155                 160
Gln Arg Pro Asn Ala Arg Leu Asn Gly Lys Val Gln Leu Asn Leu
                165                 170                 175
Met Asp Leu Val Ser Gly Ile Pro Ala Thr Gln Ser Gln Lys Ile Gln
            180                 185                 190
Glu Val Gly Glu Ile Thr Asn Leu Arg Val Asn Phe Thr Arg Leu Ala
            195                 200                 205
Pro Val Pro Lys Leu Asp His Pro Pro Ser Ala Tyr Tyr Ala Val Ser
            210                 215                 220
Gln Leu Arg Leu Gln Gly Ser Cys Phe Cys His Gly His Ala Asp Arg
225                 230                 235                 240
Cys Ala Pro Lys Pro Gly Ala Ser Ala Gly Ser Thr Ala Val Gln Val
                245                 250                 255
His Asp Val Cys Val Cys Gln His Asn Thr Ala Gly Pro Asn Cys Glu
            260                 265                 270
Arg Cys Ala Pro Phe Tyr Asn Asn Arg Pro Trp Arg Pro Ala Glu Gly
            275                 280                 285
Gln Asp Ala His Glu Cys Gln Arg Cys Asp Cys Asn Gly His Ser Glu
            290                 295                 300
Asn Cys His Phe Asp Pro Ala Val Phe Ala Ala Ser Gln Gly Ala Tyr
305                 310                 315                 320
Gly Gly Val Cys Asp Asn Cys Arg Asp His Thr Glu Gly Lys Asn Cys
                325                 330                 335
Glu Arg Cys Gln Leu His Tyr Phe Arg Asn Arg Arg Pro Gly Ala Ser
            340                 345                 350
Ile Gln Glu Thr Cys Ile Ser Cys Glu Cys Asp Pro Asp Gly Gln Trp
            355                 360                 365
Ala Gly Ala Pro Cys Asp Pro Val Thr Gly Gln Cys Val Cys Lys Glu
            370                 375                 380
His Val Gln Gly Glu Arg Cys Asp Leu Cys Lys Pro Gly Phe Thr Gly
385                 390                 395                 400
Leu Thr Tyr Ala Asn Pro Gln Gly Cys His Arg Cys Asp Cys Asn Ile
                405                 410                 415
Leu Pro Ser Arg Arg Leu Pro Cys Asp Glu Glu Ser Gly Arg Cys Leu
            420                 425                 430
Cys Leu Pro Asn Val Gly Gly Pro Lys Cys Asp Gln Cys Ala Pro Tyr
            435                 440                 445
His Trp Lys Leu Ala Ser Gly Gln Gly Cys Glu Pro Cys Ala Cys Asp
            450                 455                 460
Pro His Asn Ser Leu Ser Pro Gln Cys Asn Gln Phe Thr Gly Gln Cys
465                 470                 475                 480
Pro Cys Arg Glu Gly Phe Gly Gly Leu Met Cys Ser Ala Ala Ala Ile
                485                 490                 495
Arg Gln Cys Pro Asp Arg Thr Tyr Gly Asp Val Ala Thr Gly Cys Arg
            500                 505                 510
```

-continued

| | | | | | | | | | | | |
|---|---|---|---|---|---|---|---|---|---|---|---|
|Ala|Cys|Asp|Cys|Asp|Phe|Arg|Gly|Thr|Glu|Gly|Pro|Gly|Cys|Asp|Lys|
| |515| | | |520| | | |525| | |

Ala Cys Asp Cys Asp Phe Arg Gly Thr Glu Gly Pro Gly Cys Asp Lys
    515                 520                 525

Ala Ser Gly Val Leu Cys Arg Pro Gly Leu Thr Gly Pro Arg Cys Asp
    530                 535                 540

Gln Cys Arg Gly Tyr Cys Asn Arg Tyr Pro Val Cys Val Ala Cys His
545                 550                 555                 560

Pro Cys Phe Gln Thr Tyr Asp Ala Asp Leu Arg Glu Gln Ala Leu Arg
                565                 570                 575

Phe Gly Arg Leu Pro Asn Ala Thr Ala Ser Leu Trp Ser Gly Pro Gly
            580                 585                 590

Leu Glu Asp Arg Gly Leu Ala Ser Arg Ile Leu Asp Ala Lys Ser Lys
        595                 600                 605

Ile Glu Gln Ile Arg Ala Val Leu Ser Ser Pro Ala Val Thr Glu Gln
610                 615                 620

Glu Val Ala Gln Val Ala Ser Ala Ile Leu Ser Leu Arg Arg Thr Leu
625                 630                 635                 640

Gln Gly Leu Gln Leu Asp Leu Pro Leu Glu Glu Thr Leu Ser Leu
                645                 650                 655

Pro Arg Asp Leu Glu Ser Leu Asp Arg Ser Phe Asn Gly Leu Leu Thr
            660                 665                 670

Met Tyr Gln Arg Lys Arg Glu Gln Phe Glu Lys Ile Ser Ser Ala Asp
        675                 680                 685

Pro Ser Gly Ala Phe Arg Met Leu Ser Thr Ala Tyr Glu Gln Ser Ala
    690                 695                 700

Gln Ala Ala Gln Gln Val Ser Asp Ser Ser Arg Leu Leu Asp Gln Leu
705                 710                 715                 720

Arg Asp Ser Arg Arg Glu Ala Glu Arg Leu Val Arg Gln Ala Gly Gly
                725                 730                 735

Gly Gly Gly Thr Gly Ser Pro Lys Leu Val Ala Leu Arg Leu Glu Met
            740                 745                 750

Ser Ser Leu Pro Asp Leu Thr Pro Thr Phe Asn Lys Leu Cys Gly Asn
        755                 760                 765

Ser Arg Gln Met Ala Cys Thr Pro Ile Ser Cys Pro Gly Glu Leu Cys
    770                 775                 780

Pro Gln Asp Asn Gly Thr Ala Cys Ala Ser Arg Cys Arg Gly Val Leu
785                 790                 795                 800

Pro Arg Ala Gly Gly Ala Phe Leu Met Ala Gly Gln Val Ala Glu Gln
                805                 810                 815

Leu Arg Ala Ser Met Pro Ala Pro Ala Thr Arg Gln Met Ile Arg Ala
            820                 825                 830

Ala Glu Glu Ser Ala Ser Gln Ile Gln Ser Ser Ala Gln Arg Leu Glu
        835                 840                 845

Thr Gln Val Ser Ala Ser Arg Ser Gln Met Glu Glu Asp Val Arg Arg
    850                 855                 860

Thr Arg Leu Leu Ile Gln Gln Val Arg Asp Phe Leu Thr Asp Pro Asp
865                 870                 875                 880

Thr Asp Ala Ala Thr Ile Gln Glu Val Arg Arg Ala Val Leu Ala Leu
                885                 890                 895

Trp Leu Pro Thr Asp Ser Ala Thr Val Leu Gln Lys Met Asn Glu Ile
            900                 905                 910

Gln Ala Ile Ala Ala Arg Leu Pro Asn Val Asp Leu Val Leu Ser Gln
        915                 920                 925

Thr Lys Gln Asp Ile Gly Gly Ala Arg Arg Leu Gln Ala Glu Ala Glu

```
                  930             935             940
Glu Ala Arg Ser Arg Ala His Ala Val Glu Gly Gln Val Glu Asp Val
945                 950                 955                 960

Val Gly Asn Leu Arg Gln Gly Thr Val Ala Leu Gln Glu Ala Gln Asp
                965                 970                 975

Thr Met Gln Gly Thr Ser Arg Ser Leu Arg Leu Ile Gln Asp Arg Val
            980                 985                 990

Ala Glu Val Gln Gln Val Leu Gly Gln Gln Lys Leu Val Thr Ser Met
        995                 1000                1005

Thr Lys Gln Leu Gly Asp Phe Trp Thr Arg Met Glu Glu Leu Arg His
    1010                1015                1020

Gln Ala Arg Gln Gln Gly Ala Glu Ala Val Gln Ala Gln Gln Leu Ala
1025                1030                1035                1040

Glu Gly Ala Ser Glu Gln Ala Leu Ser Ala Gln Glu Gly Phe Glu Arg
                1045                1050                1055

Ile Lys Gln Lys Tyr Ala Glu Leu Lys Asp Arg Leu Gly Gln Ser Ser
                1060                1065                1070

Met Leu Gly Glu Gln Gly Ala Arg Ile Gln Ser Val Lys Thr Glu Ala
            1075                1080                1085

Glu Glu Leu Phe Gly Glu Thr Met Glu Met Met Asp Arg Met Lys Asp
    1090                1095                1100

Met Glu Leu Glu Leu Leu Arg Ala Ala Gly His His Ala Ala Leu Ser
1105                1110                1115                1120

Asp Leu Thr Gly Leu Glu Lys Arg Val Glu Gln Ile Arg Asp His Ile
                1125                1130                1135

Asn Gly Arg Val Leu Tyr Tyr Ser Thr Cys Lys
            1140                1145

<210> SEQ ID NO 4
<211> LENGTH: 1196
<212> TYPE: PRT
<213> ORGANISM: Artificial Sequence
<220> FEATURE:
<221> NAME/KEY: DOMAIN
<222> LOCATION: (1)...(250)
<223> OTHER INFORMATION: Human B1 chain
<220> FEATURE:
<221> NAME/KEY: DOMAIN
<222> LOCATION: (251)...(437)
<223> OTHER INFORMATION: Human B1 chain
<220> FEATURE:
<221> NAME/KEY: DOMAIN
<222> LOCATION: (438)...(807)
<223> OTHER INFORMATION: Human B1 chain
<220> FEATURE:
<221> NAME/KEY: DOMAIN
<222> LOCATION: (808)...(840)
<223> OTHER INFORMATION: Human B1 chain
<220> FEATURE:
<221> NAME/KEY: DOMAIN
<222> LOCATION: (841)...(1196)
<223> OTHER INFORMATION: Human B1 chain

<400> SEQUENCE: 4

Gln Glu Pro Glu Phe Ser Tyr Gly Cys Ala Glu Gly Ser Cys Tyr Pro
1               5                   10                  15

Ala Thr Gly Asp Leu Leu Ile Gly Arg Ala Gln Lys Leu Ser Val Thr
            20                  25                  30

Ser Thr Thr Cys Gly Leu His Lys Pro Glu Pro Tyr Cys Ile Val Ser
        35                  40                  45

His Leu Gln Glu Asp Lys Lys Cys Phe Ile Cys Asn Ser Gln Asp Pro
```

-continued

```
                50                       55                       60
Tyr His Glu Thr Leu Asn Pro Asp Ser His Leu Ile Glu Asn Val Val
 65                       70                       75                       80

Thr Thr Phe Ala Pro Asn Arg Leu Lys Ile Trp Trp Gln Ser Glu Asn
                 85                       90                       95

Gly Val Glu Asn Val Thr Ile Gln Leu Asp Leu Glu Ala Glu Phe His
                100                      105                      110

Phe Thr His Leu Ile Met Thr Phe Lys Thr Phe Arg Pro Ala Ala Met
                115                      120                      125

Leu Ile Glu Arg Ser Ser Asp Phe Gly Lys Thr Trp Gly Val Tyr Arg
130                      135                      140

Tyr Phe Ala Tyr Asp Cys Glu Ala Ser Phe Pro Gly Ile Ser Thr Gly
145                      150                      155                      160

Pro Met Lys Lys Val Asp Asp Ile Ile Cys Asp Ser Arg Tyr Ser Asp
                165                      170                      175

Ile Glu Pro Ser Thr Glu Gly Glu Val Ile Phe Arg Ala Leu Asp Pro
                180                      185                      190

Ala Phe Lys Ile Glu Asp Pro Tyr Ser Pro Arg Ile Gln Asn Leu Leu
                195                      200                      205

Lys Ile Thr Asn Leu Arg Ile Lys Phe Val Lys Leu His Thr Leu Gly
210                      215                      220

Asp Asn Leu Leu Asp Ser Arg Met Glu Ile Arg Glu Lys Tyr Tyr Tyr
225                      230                      235                      240

Ala Val Tyr Asp Met Val Val Arg Gly Asn Cys Phe Cys Tyr Gly His
                245                      250                      255

Ala Ser Glu Cys Ala Pro Val Asp Gly Phe Asn Glu Glu Val Glu Gly
                260                      265                      270

Met Val His Gly His Cys Met Cys Arg His Asn Thr Lys Gly Leu Asn
                275                      280                      285

Cys Gly Leu Cys Met Asp Phe Tyr His Asp Leu Pro Trp Arg Pro Ala
290                      295                      300

Glu Gly Arg Asn Ser Asn Ala Cys Lys Lys Cys Asn Cys Asn Glu His
305                      310                      315                      320

Ser Ile Ser Cys His Phe Asp Met Ala Val Tyr Leu Ala Thr Gly Asn
                325                      330                      335

Val Ser Gly Gly Val Cys Asp Asp Cys Gln His Asn Thr Met Gly Arg
                340                      345                      350

Asn Cys Glu Gln Cys Lys Pro Phe Tyr Tyr Gln His Pro Glu Arg Asp
                355                      360                      365

Ile Arg Asp Pro Asn Phe Cys Glu Arg Cys Thr Cys Asp Pro Ala Gly
370                      375                      380

Ser Gln Asn Glu Gly Ile Cys Asp Ser Tyr Thr Asp Phe Ser Thr Gly
385                      390                      395                      400

Leu Ile Ala Gly Gln Cys Arg Cys Lys Leu Asn Val Glu Gly Glu His
                405                      410                      415

Cys Asp Val Cys Lys Glu Gly Phe Tyr Asp Leu Ser Ser Glu Asp Pro
                420                      425                      430

Phe Gly Cys Lys Ser Cys Val Cys Asn Tyr Leu Gly Thr Val Gln Glu
                435                      440                      445

His Cys Asn Gly Ser Asp Cys Gln Cys Asp Lys Ala Thr Gly Gln Cys
                450                      455                      460

Leu Cys Leu Pro Asn Val Ile Gly Gln Asn Cys Asp Arg Cys Ala Pro
465                      470                      475                      480
```

```
Asn Thr Trp Gln Leu Ala Ser Gly Thr Gly Cys Asp Pro Cys Asn Cys
                485                 490                 495
Asn Ala Ala His Ser Phe Gly Pro Ser Cys Asn Glu Phe Thr Gly Gln
            500                 505                 510
Cys Gln Cys Met Pro Gly Phe Gly Arg Thr Cys Ser Glu Cys Gln
        515                 520                 525
Glu Leu Phe Trp Gly Asp Pro Asp Val Glu Cys Arg Ala Cys Asp Cys
    530                 535                 540
Asp Pro Arg Gly Ile Glu Thr Pro Gln Cys Asp Gln Ser Thr Gly Gln
545                 550                 555                 560
Cys Val Cys Val Glu Gly Val Glu Gly Pro Arg Cys Asp Lys Cys Thr
                565                 570                 575
Arg Gly Tyr Ser Gly Val Phe Pro Asp Cys Thr Pro Cys His Gln Cys
            580                 585                 590
Phe Ala Leu Trp Asp Val Ile Ile Ala Glu Leu Thr Asn Arg Thr His
        595                 600                 605
Arg Phe Leu Glu Lys Ala Lys Ala Leu Lys Ile Ser Gly Val Ile Gly
    610                 615                 620
Pro Tyr Arg Glu Thr Val Asp Ser Val Glu Arg Lys Val Ser Glu Ile
625                 630                 635                 640
Lys Asp Ile Leu Ala Gln Ser Pro Ala Ala Glu Pro Leu Lys Asn Ile
                645                 650                 655
Gly Asn Leu Phe Glu Glu Ala Glu Lys Leu Ile Lys Asp Val Thr Glu
            660                 665                 670
Met Met Ala Gln Val Glu Val Lys Leu Ser Asp Thr Thr Ser Gln Ser
        675                 680                 685
Asn Ser Thr Ala Lys Glu Leu Asp Ser Leu Gln Thr Glu Ala Glu Ser
    690                 695                 700
Leu Asp Asn Thr Val Lys Glu Leu Ala Glu Gln Leu Glu Phe Ile Lys
705                 710                 715                 720
Asn Ser Asp Ile Arg Gly Ala Leu Asp Ser Ile Thr Lys Tyr Phe Gln
                725                 730                 735
Met Ser Leu Glu Ala Glu Glu Arg Val Asn Ala Ser Thr Thr Glu Pro
            740                 745                 750
Asn Ser Thr Val Glu Gln Ser Ala Leu Met Arg Asp Arg Val Glu Asp
        755                 760                 765
Val Met Met Glu Arg Glu Ser Gln Phe Lys Glu Lys Gln Glu Glu Gln
    770                 775                 780
Ala Arg Leu Leu Asp Glu Leu Ala Gly Lys Leu Gln Ser Leu Asp Leu
785                 790                 795                 800
Ser Ala Ala Ala Glu Met Thr Cys Gly Thr Pro Pro Gly Ala Ser Cys
                805                 810                 815
Ser Glu Thr Glu Cys Gly Gly Pro Asn Cys Arg Thr Asp Glu Gly Glu
            820                 825                 830
Arg Lys Cys Gly Gly Pro Gly Cys Gly Gly Leu Val Thr Val Ala His
        835                 840                 845
Asn Ala Trp Gln Lys Ala Met Asp Leu Asp Gln Asp Val Leu Ser Ala
    850                 855                 860
Leu Ala Glu Val Glu Gln Leu Ser Lys Met Val Ser Glu Ala Lys Leu
865                 870                 875                 880
Arg Ala Asp Glu Ala Lys Gln Ser Ala Glu Asp Ile Leu Leu Lys Thr
                885                 890                 895
```

```
Asn Ala Thr Lys Glu Lys Met Asp Lys Ser Asn Glu Glu Leu Arg Asn
            900                 905                 910

Leu Ile Lys Gln Ile Arg Asn Phe Leu Thr Gln Asp Ser Ala Asp Leu
        915                 920                 925

Asp Ser Ile Glu Ala Val Ala Asn Glu Val Leu Lys Met Glu Met Pro
    930                 935                 940

Ser Thr Pro Gln Gln Leu Gln Asn Leu Thr Glu Asp Ile Arg Glu Arg
945                 950                 955                 960

Val Glu Ser Leu Ser Gln Val Glu Val Ile Leu Gln His Ser Ala Ala
                965                 970                 975

Asp Ile Ala Arg Ala Glu Met Leu Leu Glu Glu Ala Lys Arg Ala Ser
            980                 985                 990

Lys Ser Ala Thr Asp Val Lys Val Thr Ala Asp Met Val Lys Glu Ala
        995                 1000                1005

Leu Glu Glu Ala Glu Lys Ala Gln Val Ala Ala Glu Lys Ala Ile Lys
    1010                1015                1020

Gln Ala Asp Glu Asp Ile Gln Gly Thr Gln Asn Leu Leu Thr Ser Ile
1025                1030                1035                1040

Glu Ser Glu Thr Ala Ala Ser Glu Glu Thr Leu Phe Asn Ala Ser Gln
                1045                1050                1055

Arg Ile Ser Glu Leu Glu Arg Asn Val Glu Glu Leu Lys Arg Lys Ala
            1060                1065                1070

Ala Gln Asn Ser Gly Glu Ala Glu Tyr Ile Glu Lys Val Val Tyr Thr
        1075                1080                1085

Val Lys Gln Ser Ala Glu Asp Val Lys Lys Thr Leu Asp Gly Glu Leu
    1090                1095                1100

Asp Glu Lys Tyr Lys Lys Val Glu Asn Leu Ile Ala Lys Lys Thr Glu
1105                1110                1115                1120

Glu Ser Ala Asp Ala Arg Arg Lys Ala Glu Met Leu Gln Asn Glu Ala
                1125                1130                1135

Lys Thr Leu Leu Ala Gln Ala Asn Ser Lys Leu Gln Leu Leu Lys Asp
            1140                1145                1150

Leu Glu Arg Lys Tyr Glu Asp Asn Gln Arg Tyr Leu Asp Lys Ala
        1155                1160                1165

Gln Glu Leu Ala Arg Leu Glu Gly Glu Val Arg Ser Leu Leu Lys Asp
    1170                1175                1180

Ile Ser Gln Lys Val Ala Val Tyr Ser Thr Cys Leu
1185                1190                1195

<210> SEQ ID NO 5
<211> LENGTH: 231
<212> TYPE: PRT
<213> ORGANISM: Artificial Sequence
<220> FEATURE:
<221> NAME/KEY: DOMAIN
<222> LOCATION: (1)...(231)
<223> OTHER INFORMATION: VI of B1k

<400> SEQUENCE: 5

Gln Gln Ala Cys Ser Arg Gly Ala Cys Tyr Pro Pro Val Gly Asp Leu
1               5                   10                  15

Leu Val Gly Arg Thr Arg Phe Leu Arg Ala Ser Ser Thr Cys Gly Leu
            20                  25                  30

Thr Lys Pro Glu Thr Tyr Cys Thr Gln Tyr Gly Glu Trp Gln Met Lys
        35                  40                  45

Cys Cys Lys Cys Asn Ser Arg Gln Pro His Asn Tyr Tyr Ser His Arg
```

-continued

```
                    50                  55                  60
Val Glu Asn Val Ala Ser Ser Gly Pro Met Arg Trp Trp Gln Ser
 65                  70                  75                  80

Gln Asn Asp Val Asn Pro Val Ser Leu Gln Leu Asp Leu Asp Arg Arg
                 85                  90                  95

Phe Gln Leu Gln Glu Val Met Met Glu Phe Pro Gly Ala His Ala Ala
                100                 105                 110

Gly Met Leu Ile Glu Arg Ser Ser Asp Phe Gly Lys Thr Trp Arg Val
                115                 120                 125

Tyr Gln Tyr Leu Ala Ala Asp Cys Thr Ser Thr Phe Pro Arg Val Arg
130                 135                 140

Gln Gly Arg Pro Gln Ser Trp Gln Asp Val Arg Cys Gln Ser Leu Pro
145                 150                 155                 160

Gln Arg Pro Asn Ala Arg Leu Asn Gly Gly Lys Val Gln Leu Asn Leu
                165                 170                 175

Met Asp Leu Val Ser Gly Ile Glu Ala Thr Gln Ser Gln Lys Ile Gln
                180                 185                 190

Glu Val Gly Glu Ile Thr Asn Leu Arg Ile Lys Phe Val Lys Leu Ala
                195                 200                 205

Pro Val Pro Lys Leu Asp His Pro Pro Ser Ala Tyr Tyr Ala Val Ser
                210                 215                 220

Gln Leu Arg Leu Gln Gly Ser
225                 230
```

<210> SEQ ID NO 6
<211> LENGTH: 249
<212> TYPE: PRT
<213> ORGANISM: Artificial Sequence
<220> FEATURE:
<221> NAME/KEY: DOMAIN
<222> LOCATION: (1)...(249)
<223> OTHER INFORMATION: VI of B1e

<400> SEQUENCE: 6

```
Gln Glu Pro Glu Phe Ser Tyr Gly Cys Ala Glu Gly Ser Cys Tyr Pro
 1               5                  10                  15

Ala Thr Gly Asp Leu Leu Ile Gly Arg Ala Gln Lys Leu Ser Val Thr
                 20                  25                  30

Ser Thr Cys Gly Leu His Lys Pro Glu Pro Tyr Cys Ile Val Ser His
                 35                  40                  45

Leu Gln Glu Asp Lys Lys Cys Phe Ile Cys Asn Ser Gln Asp Pro Tyr
                 50                  55                  60

His Glu Thr Leu Asn Pro Asp Ser His Leu Ile Glu Asn Val Val Thr
 65                  70                  75                  80

Thr Phe Ala Pro Asn Arg Leu Lys Ile Trp Trp Gln Ser Glu Asn Gly
                 85                  90                  95

Val Glu Asn Val Thr Ile Gln Leu Asp Leu Glu Ala Glu Phe His Phe
                100                 105                 110

Thr His Leu Ile Met Thr Phe Lys Thr Phe Arg Pro Ala Ala Met Leu
                115                 120                 125

Ile Glu Arg Ser Ser Asp Phe Gly Lys Thr Trp Gly Val Tyr Arg Tyr
130                 135                 140

Phe Ala Tyr Asp Cys Glu Ala Ser Phe Pro Gly Ile Ser Thr Gly Pro
145                 150                 155                 160

Met Lys Lys Val Asp Asp Ile Ile Cys Asp Ser Arg Tyr Ser Asp Ile
                165                 170                 175
```

-continued

```
Glu Pro Ser Thr Glu Gly Glu Val Ile Phe Arg Ala Leu Asp Pro Ala
180 185 190

Phe Lys Ile Glu Asp Pro Tyr Ser Pro Arg Ile Gln Asn Leu Leu Lys
195 200 205

Ile Thr Asn Leu Arg Ile Lys Phe Val Lys Leu His Thr Leu Gly Asp
210 215 220

Asn Leu Leu Asp Ser Arg Met Glu Ile Arg Glu Lys Tyr Tyr Tyr Ala
225 230 235 240

Val Tyr Asp Met Val Val Arg Gly Asn
245

<210> SEQ ID NO 7
<211> LENGTH: 250
<212> TYPE: PRT
<213> ORGANISM: Artificial Sequence
<220> FEATURE:
<221> NAME/KEY: DOMAIN
<222> LOCATION: (1)...(250)
<223> OTHER INFORMATION: VI of B1g

<400> SEQUENCE: 7

Gln Val Pro Ser Leu Asp Val Pro Gly Cys Ser Arg Gly Ser Cys Tyr
1 5 10 15

Pro Ala Thr Gly Asp Leu Leu Val Gly Arg Ala Asp Arg Leu Thr Ala
20 25 30

Ser Ser Thr Cys Gly Leu His Ser Pro Gln Pro Tyr Cys Ile Val Ser
35 40 45

His Leu Gln Asp Glu Lys Lys Cys Phe Leu Cys Asp Ser Arg Arg Pro
50 55 60

Phe Ser Ala Arg Asp Asn Pro Asn Ser His Arg Ile Gln Asn Val Val
65 70 75 80

Thr Ser Phe Ala Pro Gln Arg Arg Thr Ala Trp Trp Gln Ser Glu Asn
85 90 95

Gly Val Pro Met Val Thr Ile Gln Leu Asp Leu Glu Ala Glu Phe His
100 105 110

Phe Thr His Leu Ile Met Thr Phe Lys Thr Phe Arg Pro Ala Ala Met
115 120 125

Leu Val Glu Arg Ser Ala Asp Phe Gly Arg Thr Trp Arg Val Tyr Arg
130 135 140

Tyr Phe Ser Tyr Asp Cys Gly Ala Asp Phe Pro Gly Ile Pro Leu Ala
145 150 155 160

Pro Pro Arg Arg Trp Asp Asp Val Val Cys Glu Ser Arg Tyr Ser Glu
165 170 175

Ile Glu Pro Ser Thr Glu Gly Glu Val Ile Tyr Arg Val Leu Asp Pro
180 185 190

Ala Ile Pro Ile Pro Asp Pro Tyr Ser Ser Arg Ile Gln Asn Leu Leu
195 200 205

Lys Ile Thr Asn Leu Arg Val Asn Leu Thr Arg Leu His Thr Leu Gly
210 215 220

Asp Asn Leu Leu Asp Pro Arg Arg Glu Ile Arg Glu Lys Tyr Tyr Tyr
225 230 235 240

Ala Leu Tyr Glu Leu Val Ile Arg Gly Asn
245 250

<210> SEQ ID NO 8
<211> LENGTH: 40

```
<212> TYPE: PRT
<213> ORGANISM: Rattus rattus

<400> SEQUENCE: 8

Glu Ala Leu Lys Leu Lys Arg Ala Gly Asn Ser Leu Ala Ala Ser Thr
 1               5                  10                  15
Ala Glu Glu Thr Ala Gly Ser Ala Gln Ser Arg Ala Arg Glu Ala Glu
            20                  25                  30
Lys Gln Leu Arg Glu Gln Val Gly
        35                  40

<210> SEQ ID NO 9
<211> LENGTH: 24
<212> TYPE: PRT
<213> ORGANISM: Homo sapiens

<400> SEQUENCE: 9

Ala Gly Asn Ser Leu Ala Ala Ser Thr Ala Glu Glu Thr Ala Gly Ser
 1               5                  10                  15
Ala Gln Gly Arg Ala Gln Glu Ala
            20

<210> SEQ ID NO 10
<211> LENGTH: 40
<212> TYPE: PRT
<213> ORGANISM: Homo sapiens

<400> SEQUENCE: 10

Glu Glu Leu Arg His Gln Ala Arg Gln Gln Gly Ala Glu Ala Val Gln
 1               5                  10                  15
Ala Gln Gln Leu Ala Glu Gly Ala Ser Glu Gln Ala Leu Ser Ala Gln
            20                  25                  30
Glu Gly Phe Glu Arg Ile Lys Gln
        35                  40

<210> SEQ ID NO 11
<211> LENGTH: 40
<212> TYPE: PRT
<213> ORGANISM: Homo sapiens

<400> SEQUENCE: 11

Thr Gly Asp Cys Tyr Ser Gly Asp Glu Asn Pro Asp Ile Glu Cys Ala
 1               5                  10                  15
Asp Cys Pro Ile Gly Phe Tyr Asn Asp Pro His Asp Pro Arg Ser Cys
            20                  25                  30
Lys Pro Cys Pro Cys His Asn Gly
        35                  40

<210> SEQ ID NO 12
<211> LENGTH: 17
<212> TYPE: PRT
<213> ORGANISM: Homo sapiens

<400> SEQUENCE: 12

Asp Glu Asn Pro Asp Ile Glu Cys Ala Asp Cys Pro Ile Gly Phe Tyr
 1               5                  10                  15
Asn

<210> SEQ ID NO 13
<211> LENGTH: 40
<212> TYPE: PRT
```

```
-continued

<213> ORGANISM: Homo sapiens

<400> SEQUENCE: 13

Lys Val Asp Thr Arg Ala Lys Asn Ala Gly Val Thr Ile Gln Asp Thr
  1               5                  10                  15

Leu Asn Thr Leu Asp Gly Leu Leu His Leu Met Asp Gln Pro Leu Ser
             20                  25                  30

Val Asp Glu Glu Gly Leu Val Leu
         35                  40

<210> SEQ ID NO 14
<211> LENGTH: 25
<212> TYPE: PRT
<213> ORGANISM: Homo sapiens

<400> SEQUENCE: 14

Asn Ala Gly Val Thr Ile Gln Asp Thr Leu Asn Thr Leu Asp Gly Leu
  1               5                  10                  15

Leu His Leu Met Asp Gln Pro Leu Ser
             20                  25
```

What is claimed is:

1. An isolated monoclonal antibody that binds to domain VI of SEQ ID NO:2.

2. The An isolated monoclonal antibody that binds to domain III of SEQ ID NO:2.

3. An isolated monoclonal antibody that binds to domain II of SEQ ID NO:2.

4. An isolated monoclonal antibody that binds to domain I of SEQ ID NO:2.

5. An isolated monoclonal antibody that binds to domain alpha of SEQ ID NO:2.

6. An isolated monoclonal antibody that binds to EGF domains 2, 3, 4, 5 or 6 of SEQ ID NO:2.

7. The monoclonal antibody of claim 1 wherein the antibody is a mouse monoclonal antibody.

8. A method for making a domain-specific antibody, the method comprising:
   immunizing an experimental animal with an immunogen comprising an isolated polypeptide that consists of an amino acid sequence of a domain of SEQ ID NO:2 or a fragment of the domain, wherein the domain is selected from the group consisting of:
   (a) domain VI,
   (b) domain III/V,
   (c) domain II,
   (d) domain I,
   (e) domain alpha,
   (f) EGF domain 1,
   (g) EGF domain 2,
   (h) EGE domain 3,
   (i) EGF domain 4,
   (j) EGE domain 5 and,
   (k) EGF domain 6; and
   preparing, from the experimental animal, an antibody that binds to the immunogen.

9. The method of claim 8, wherein the immunogen is a polypeptide consisting of domain VI of SEQ ID NO:2 or an immunogenic fragment thereof.

10. The method of claim 8, wherein the immunogen is a polypeptide consisting of domain III/V of SEQ ID NO:2 or an immunogenic fragment thereof.

11. The method of claim 8, wherein the immunogen is a polypeptide consisting of domain II of SEQ ID NO:2 or an antigenic fragment thereof.

12. The method of claim 8, wherein the immunogen is a polypeptide consisting of domain I of SEQ ID NO:2 or an antigenic fragment thereof.

13. The method of claim 8, wherein the immunogen is a polypeptide consisting of domain alpha of SEQ ID NO:2 or an antigenic fragment thereof.

14. The method of claim 8, wherein the immunogen is a polypeptide consisting of any one of EGF domains 1, 2, 3, 4, 5 or 6 SEQ ID NO:2 or an antigenic fragment thereof.

15. The method of any one of claims 8–14, wherein the animal is a mouse.

16. The method of any one of claims 8–14, wherein the antibody is a monoclonal antibody.

17. The monoclonal antibody of claim 2 wherein the antibody is a mouse monoclonal antibody.

18. The monoclonal antibody of claim 3 wherein the antibody is a mouse monoclonal antibody.

19. The monoclonal antibody of claim 4 wherein the antibody is a mouse monoclonal antibody.

20. The monoclonal antibody of claim 5 wherein the antibody is a mouse monoclonal antibody.

21. The monoclonal antibody of claim 6 wherein the antibody is a mouse monoclonal antibody.

22. The monoclonal antibody of claim 7 wherein the antibody is a mouse monoclonal antibody.

23. A substantially pure preparation comprising a monoclonal antibody according to claim 1.

24. A substantially pure preparation comprising a monoclonal antibody according to claim 2.

25. A substantially pure preparation comprising a monoclonal antibody according to claim 3.

26. A substantially pure preparation comprising a monoclonal antibody according to claim 4.

27. A substantially pure preparation comprising a monoclonal antibody according to claim 5.

28. A substantially pure preparation comprising a monoclonal antibody according to claim 6.

29. A substantially pure preparation comprising a monoclonal antibody according to claim 7.

* * * * *

UNITED STATES PATENT AND TRADEMARK OFFICE
CERTIFICATE OF CORRECTION

PATENT NO. : 6,916,631 B2
DATED : July 12, 2005
INVENTOR(S) : Robert Eugene Burgeson et al.

It is certified that error appears in the above-identified patent and that said Letters Patent is hereby corrected as shown below:

Title page,
Item [56], References Cited, U.S. PATENT DOCUMENTS, insert:
-- U.S. Appl. No. 08/141,233, filed Oct. 1993, Burgeson et al. --.
OTHER PUBLICATIONS,
"Gerecke" reference, replace "Proein" with -- Protein --; and
delete "U.S. Appl. No. 08/141,233, filed Oct. 1993, Burgeson et al.".

Column 49,
Line 30, before "An" delete "The".

Column 50,
Line 35, between "6" and "SEQ" insert -- of --.

Signed and Sealed this

Fourth Day of April, 2006

JON W. DUDAS
*Director of the United States Patent and Trademark Office*